United States Patent
Sapre

(10) Patent No.: US 10,271,840 B2
(45) Date of Patent: Apr. 30, 2019

(54) APPARATUS AND METHOD FOR DIFFERENTIATING BETWEEN TISSUE AND MECHANICAL OBSTRUCTION IN A SURGICAL INSTRUMENT

(71) Applicant: Covidien LP, Mansfield, MA (US)

(72) Inventor: Parag Sapre, Yardley, PA (US)

(73) Assignee: Covidien LP, Mansfield, MA (US)

( * ) Notice: Subject to any disclaimer, the term of this patent is extended or adjusted under 35 U.S.C. 154(b) by 396 days.

(21) Appl. No.: 14/463,164

(22) Filed: Aug. 19, 2014

(65) Prior Publication Data
US 2015/0080912 A1 Mar. 19, 2015

Related U.S. Application Data

(60) Provisional application No. 61/879,445, filed on Sep. 18, 2013.

(51) Int. Cl.
*A61B 17/068* (2006.01)
*A61B 17/072* (2006.01)
(Continued)

(52) U.S. Cl.
CPC ...... *A61B 17/068* (2013.01); *A61B 17/07207* (2013.01); *A61B 90/03* (2016.02);
(Continued)

(58) Field of Classification Search
CPC .... A61B 17/07207; A61B 2017/00017; A61B 17/068; A61B 2017/00039; A61B 2017/00221; A61B 19/46
(Continued)

(56) References Cited

U.S. PATENT DOCUMENTS 2,245,994 A 6/1941 McWane
2,777,340 A 1/1957 Hettwer et al.
(Continued)

FOREIGN PATENT DOCUMENTS

AU 2008229795 A1 4/2009
CA 2451558 A1 1/2003
(Continued)

OTHER PUBLICATIONS

Chinese Office Action dated Oct. 24, 2017 in corresponding Chinese Patent Application No. 201410479971.9 together with English translation, 12 pages.
(Continued)

*Primary Examiner* — Robert Long

(57) ABSTRACT

A surgical instrument is provided. The surgical instrument includes: a handle assembly; a jaw assembly comprising a staple cartridge containing a plurality of staples and an anvil to form the plurality of staples upon firing; a drive assembly at least partially located within the handle and connected to the jaw assembly and the lockout mechanism; a motor disposed within the handle assembly and operatively coupled to the drive assembly; and a controller operatively coupled to the motor, the controller configured to control supply of electrical current to the motor and to monitor a current draw of the motor, wherein the controller is further configured to terminate the supply of electrical current to the motor in response to a rate of change of the current draw indicative of a mechanical limit of at least one of the jaw assembly, the drive assembly, or the motor.

7 Claims, 13 Drawing Sheets

(51) Int. Cl.
  *A61B 17/00* (2006.01)
  *A61B 90/00* (2016.01)
(52) U.S. Cl.
  CPC .............. *A61B 2017/00017* (2013.01); *A61B 2017/0046* (2013.01); *A61B 2017/00115* (2013.01); *A61B 2017/00137* (2013.01); *A61B 2017/00398* (2013.01); *A61B 2017/00473* (2013.01); *A61B 2017/00734* (2013.01); *A61B 2090/0803* (2016.02); *A61B 2090/0804* (2016.02); *A61B 2090/0811* (2016.02)
(58) Field of Classification Search
  USPC .......................................... 227/175.1–182.1
  See application file for complete search history.

(56) References Cited

U.S. PATENT DOCUMENTS

| | | | |
|---|---|---|---|
| 2,957,353 A | 10/1960 | Babacz | |
| 2,961,808 A * | 11/1960 | Dunigan | B23Q 15/225 451/26 |
| 3,111,328 A | 11/1963 | Di Rito et al. | |
| 3,695,058 A | 10/1972 | Keith, Jr. | |
| 3,734,515 A | 5/1973 | Dudek | |
| 3,759,336 A | 9/1973 | Marcovitz et al. | |
| 4,072,888 A * | 2/1978 | Bechtle | H02P 8/14 318/685 |
| 4,162,399 A | 7/1979 | Hudson | |
| 4,606,343 A | 8/1986 | Conta et al. | |
| 4,705,038 A | 11/1987 | Sjostrom et al. | |
| 4,722,685 A | 2/1988 | de Estrada et al. | |
| 4,823,807 A | 4/1989 | Russell et al. | |
| 4,874,181 A | 10/1989 | Hsu | |
| 5,129,118 A | 7/1992 | Walmesley | |
| 5,129,570 A | 7/1992 | Schulze et al. | |
| 5,152,744 A | 10/1992 | Krause et al. | |
| 5,301,061 A | 4/1994 | Nakada et al. | |
| 5,312,023 A | 5/1994 | Green et al. | |
| 5,326,013 A | 7/1994 | Green et al. | |
| 5,350,355 A | 9/1994 | Sklar | |
| 5,383,874 A | 1/1995 | Jackson et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,400,267 A | 3/1995 | Denen et al. | |
| 5,411,508 A | 5/1995 | Bessler et al. | |
| 5,413,267 A | 5/1995 | Solyntjes et al. | |
| 5,427,087 A | 6/1995 | Ito et al. | |
| 5,467,911 A | 11/1995 | Tsuruta et al. | |
| 5,476,379 A | 12/1995 | Disel | |
| 5,487,499 A | 1/1996 | Sorrentino et al. | |
| 5,518,163 A | 5/1996 | Hooven | |
| 5,518,164 A | 5/1996 | Hooven | |
| 5,526,822 A | 6/1996 | Burbank et al. | |
| 5,529,235 A | 6/1996 | Boiarski et al. | |
| 5,530,788 A * | 6/1996 | Saijima | H02H 7/0838 318/434 |
| 5,535,934 A | 7/1996 | Boiarski et al. | |
| 5,535,937 A | 7/1996 | Boiarski et al. | |
| 5,540,375 A | 7/1996 | Bolanos et al. | |
| 5,540,706 A | 7/1996 | Aust et al. | |
| 5,542,594 A | 8/1996 | McKean et al. | |
| 5,549,637 A | 8/1996 | Crainich | |
| 5,553,675 A | 9/1996 | Pitzen et al. | |
| 5,562,239 A | 10/1996 | Boiarski et al. | |
| 5,564,615 A | 10/1996 | Bishop et al. | |
| 5,609,560 A | 3/1997 | Ichikawa et al. | |
| 5,632,432 A | 5/1997 | Schulze et al. | |
| 5,647,526 A | 7/1997 | Green et al. | |
| 5,653,374 A | 8/1997 | Young et al. | |
| 5,658,300 A | 8/1997 | Bito et al. | |
| 5,667,517 A | 9/1997 | Hooven | |
| 5,693,042 A | 12/1997 | Boiarski et al. | |
| 5,704,534 A | 1/1998 | Huitema et al. | |
| 5,713,505 A | 2/1998 | Huitema | |
| 5,762,603 A | 6/1998 | Thompson | |
| 5,779,130 A | 7/1998 | Alesi et al. | |
| 5,782,396 A | 7/1998 | Mastri et al. | |
| 5,782,397 A | 7/1998 | Koukline | |
| 5,797,536 A | 8/1998 | Smith et al. | |
| 5,820,009 A | 10/1998 | Melling et al. | |
| 5,863,159 A | 1/1999 | Lasko | |
| 5,865,361 A | 2/1999 | Milliman et al. | |
| 5,878,607 A * | 3/1999 | Nunes | A61F 15/02 30/124 |
| 5,908,427 A | 6/1999 | McKean et al. | |
| 5,954,259 A | 9/1999 | Viola et al. | |
| 5,964,774 A | 10/1999 | McKean et al. | |
| 5,993,454 A | 11/1999 | Longo | |
| 6,010,054 A | 1/2000 | Johnson et al. | |
| 6,017,354 A | 1/2000 | Culp et al. | |
| 6,032,849 A | 3/2000 | Mastri et al. | |
| 6,045,560 A | 4/2000 | McKean et al. | |
| 6,086,544 A * | 7/2000 | Hibner | A61B 10/0275 600/564 |
| 6,090,123 A | 7/2000 | Culp et al. | |
| 6,126,651 A | 10/2000 | Mayer | |
| 6,129,547 A | 10/2000 | Cise et al. | |
| 6,165,169 A | 12/2000 | Panescu et al. | |
| 6,239,732 B1 | 5/2001 | Cusey | |
| 6,241,139 B1 | 6/2001 | Milliman et al. | |
| 6,264,086 B1 | 7/2001 | McGuckin, Jr. | |
| 6,264,087 B1 | 7/2001 | Whitman | |
| 6,302,311 B1 | 10/2001 | Adams et al. | |
| 6,315,184 B1 | 11/2001 | Whitman | |
| 6,321,855 B1 | 11/2001 | Barnes | |
| 6,329,778 B1 | 12/2001 | Culp et al. | |
| 6,343,731 B1 | 2/2002 | Adams et al. | |
| 6,348,061 B1 | 2/2002 | Whitman | |
| 6,368,324 B1 | 4/2002 | Dinger et al. | |
| 6,371,909 B1 | 4/2002 | Hoeg et al. | |
| 6,434,507 B1 | 8/2002 | Clayton et al. | |
| 6,443,973 B1 | 9/2002 | Whitman | |
| 6,461,372 B1 | 10/2002 | Jensen et al. | |
| 6,488,197 B1 | 12/2002 | Whitman | |
| 6,491,201 B1 | 12/2002 | Whitman | |
| 6,533,157 B1 | 3/2003 | Whitman | |
| 6,537,280 B2 | 3/2003 | Dinger et al. | |
| 6,610,066 B2 | 8/2003 | Dinger et al. | |
| 6,611,793 B1 | 8/2003 | Burnside et al. | |
| 6,645,218 B1 | 11/2003 | Cassidy et al. | |
| 6,654,999 B2 | 12/2003 | Stoddard et al. | |
| 6,698,643 B2 | 3/2004 | Whitman | |
| 6,699,177 B1 | 3/2004 | Wang et al. | |
| 6,716,233 B1 | 4/2004 | Whitman | |
| 6,743,240 B2 | 6/2004 | Smith et al. | |
| 6,783,533 B2 | 8/2004 | Green et al. | |
| 6,792,390 B1 | 9/2004 | Burnside et al. | |
| 6,793,652 B1 | 9/2004 | Whitman et al. | |
| 6,817,508 B1 | 11/2004 | Racenet et al. | |
| 6,830,174 B2 | 12/2004 | Hillstead et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,899,538 B2 | 5/2005 | Matoba | |
| 6,905,057 B2 | 6/2005 | Swayze et al. | |
| 6,959,852 B2 | 11/2005 | Shelton, IV et al. | |
| 6,964,363 B2 | 11/2005 | Wales et al. | |
| 6,981,628 B2 | 1/2006 | Wales | |
| 6,981,941 B2 | 1/2006 | Whitman et al. | |
| 6,986,451 B1 | 1/2006 | Mastri et al. | |
| 6,988,649 B2 | 1/2006 | Shelton, IV et al. | |
| 7,032,798 B2 | 4/2006 | Whitman et al. | |
| RE39,152 E | 6/2006 | Aust et al. | |
| 7,055,731 B2 | 6/2006 | Shelton, IV et al. | |
| 7,059,508 B2 | 6/2006 | Shelton, IV et al. | |
| 7,077,856 B2 | 7/2006 | Whitman | |
| 7,091,683 B1 | 8/2006 | Smith et al. | |
| 7,111,769 B2 | 9/2006 | Wales et al. | |
| 7,122,029 B2 | 10/2006 | Koop et al. | |
| 7,140,528 B2 | 11/2006 | Shelton, IV | |
| 7,143,923 B2 | 12/2006 | Shelton, IV et al. | |
| 7,143,925 B2 | 12/2006 | Shelton, IV et al. | |

(56) References Cited

U.S. PATENT DOCUMENTS

| | | |
|---|---|---|
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,281,681 B2 * | 10/2012 | Kimura .................. F16H 61/12 |
| | | 74/335 |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,684,253 B2 * | 4/2014 | Giordano ......... A61B 17/00234 |
| | | 227/180.1 |
| 8,696,552 B2 | 4/2014 | Whitman |
| 8,708,213 B2 | 4/2014 | Shelton, IV et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0066858 A1 * | 4/2003 | Holgersson ............... B27F 7/36 |
| | | 227/2 |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2005/0055795 A1 * | 3/2005 | Zeiler ....................... A47L 5/14 |
| | | 15/353 |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |

(56) References Cited

U.S. PATENT DOCUMENTS

| | | | |
|---|---|---|---|
| 2006/0273135 A1* | 12/2006 | Beetel | A61B 17/068 227/175.1 |
| 2006/0278680 A1 | 12/2006 | Viola et al. | |
| 2007/0023476 A1 | 2/2007 | Whitman et al. | |
| 2007/0023477 A1 | 2/2007 | Whitman et al. | |
| 2007/0029363 A1 | 2/2007 | Popov | |
| 2007/0049435 A1 | 3/2007 | Jinno et al. | |
| 2007/0055219 A1 | 3/2007 | Whitman et al. | |
| 2007/0084897 A1 | 4/2007 | Shelton et al. | |
| 2007/0102472 A1 | 5/2007 | Shelton | |
| 2007/0152014 A1 | 7/2007 | Gillum et al. | |
| 2007/0175947 A1 | 8/2007 | Ortiz et al. | |
| 2007/0175949 A1 | 8/2007 | Shelton et al. | |
| 2007/0175950 A1 | 8/2007 | Shelton et al. | |
| 2007/0175951 A1 | 8/2007 | Shelton et al. | |
| 2007/0175955 A1 | 8/2007 | Shelton et al. | |
| 2007/0175961 A1 | 8/2007 | Shelton et al. | |
| 2007/0270790 A1* | 11/2007 | Smith | A61B 17/115 606/32 |
| 2008/0029570 A1 | 2/2008 | Shelton et al. | |
| 2008/0029573 A1 | 2/2008 | Shelton et al. | |
| 2008/0029574 A1 | 2/2008 | Shelton et al. | |
| 2008/0029575 A1 | 2/2008 | Shelton et al. | |
| 2008/0058801 A1 | 3/2008 | Taylor et al. | |
| 2008/0109012 A1 | 5/2008 | Falco et al. | |
| 2008/0110958 A1 | 5/2008 | McKenna et al. | |
| 2008/0167644 A1* | 7/2008 | Shelton | A61B 17/07207 606/34 |
| 2008/0167670 A1 | 7/2008 | Shelton et al. | |
| 2008/0167671 A1* | 7/2008 | Giordano | A61B 17/07207 606/167 |
| 2008/0167736 A1 | 7/2008 | Swayze | |
| 2008/0185419 A1 | 8/2008 | Smith et al. | |
| 2008/0188841 A1 | 8/2008 | Tomasello et al. | |
| 2008/0197167 A1 | 8/2008 | Viola et al. | |
| 2008/0208195 A1 | 8/2008 | Shores et al. | |
| 2008/0237296 A1 | 10/2008 | Boudreaux et al. | |
| 2008/0251561 A1 | 10/2008 | Eades et al. | |
| 2008/0255413 A1 | 10/2008 | Zemlok et al. | |
| 2008/0255607 A1 | 10/2008 | Zemlok | |
| 2008/0262654 A1 | 10/2008 | Omori et al. | |
| 2008/0308603 A1 | 12/2008 | Shelton et al. | |
| 2009/0090763 A1 | 4/2009 | Zemlok et al. | |
| 2009/0099876 A1 | 4/2009 | Whitman | |
| 2009/0138006 A1 | 5/2009 | Bales et al. | |
| 2009/0171147 A1 | 7/2009 | Lee et al. | |
| 2009/0182193 A1 | 7/2009 | Whitman et al. | |
| 2009/0206136 A1* | 8/2009 | Moore | A61B 17/07207 227/176.1 |
| 2009/0209990 A1 | 8/2009 | Yates et al. | |
| 2009/0254094 A1 | 10/2009 | Knapp et al. | |
| 2010/0069942 A1 | 3/2010 | Shelton, IV | |
| 2010/0089970 A1* | 4/2010 | Smith | A61B 17/07207 227/175.1 |
| 2010/0117580 A1* | 5/2010 | Miwa | B25F 5/00 318/472 |
| 2010/0193568 A1 | 8/2010 | Scheib et al. | |
| 2010/0211053 A1 | 8/2010 | Ross et al. | |
| 2010/0225073 A1 | 9/2010 | Porter et al. | |
| 2010/0294829 A1* | 11/2010 | Giordano | A61B 17/00 227/176.1 |
| 2011/0006101 A1 | 1/2011 | Hall et al. | |
| 2011/0017801 A1 | 1/2011 | Zemlok et al. | |
| 2011/0071508 A1 | 3/2011 | Duval et al. | |
| 2011/0077673 A1 | 3/2011 | Grubac et al. | |
| 2011/0121049 A1 | 5/2011 | Malinouskas et al. | |
| 2011/0125138 A1 | 5/2011 | Malinouskas et al. | |
| 2011/0139851 A1 | 6/2011 | McCuen | |
| 2011/0155783 A1 | 6/2011 | Rajappa et al. | |
| 2011/0155786 A1 | 6/2011 | Shelton, IV | |
| 2011/0172648 A1 | 7/2011 | Jeong | |
| 2011/0174099 A1 | 7/2011 | Ross et al. | |
| 2011/0204119 A1 | 8/2011 | McCuen | |
| 2011/0218522 A1 | 9/2011 | Whitman | |
| 2011/0253765 A1 | 10/2011 | Nicholas et al. | |
| 2011/0276057 A1 | 11/2011 | Conlon et al. | |
| 2011/0290854 A1 | 12/2011 | Timm et al. | |
| 2011/0290855 A1 | 12/2011 | Moore et al. | |
| 2011/0295242 A1 | 12/2011 | Spivey et al. | |
| 2011/0295269 A1 | 12/2011 | Swensgard et al. | |
| 2011/0297729 A1* | 12/2011 | Whitman | A61B 17/07207 227/175.1 |
| 2012/0000962 A1 | 1/2012 | Racenet et al. | |
| 2012/0055972 A1* | 3/2012 | Marczyk | A61B 17/07207 227/175.1 |
| 2012/0074199 A1 | 3/2012 | Olson et al. | |
| 2012/0089131 A1 | 4/2012 | Zemlok et al. | |
| 2012/0104071 A1 | 5/2012 | Bryant | |
| 2012/0116368 A1 | 5/2012 | Viola | |
| 2012/0143002 A1 | 6/2012 | Aranyi et al. | |
| 2012/0172924 A1 | 7/2012 | Allen, IV | |
| 2012/0223121 A1 | 9/2012 | Viola et al. | |
| 2012/0223122 A1* | 9/2012 | Roy | A61B 17/072 227/175.1 |
| 2012/0245428 A1 | 9/2012 | Smith et al. | |
| 2012/0253329 A1 | 10/2012 | Zemlok et al. | |
| 2012/0310220 A1 | 12/2012 | Malkowski et al. | |
| 2012/0323226 A1 | 12/2012 | Chowaniec et al. | |
| 2012/0330285 A1 | 12/2012 | Hartoumbekis et al. | |
| 2013/0018361 A1 | 1/2013 | Bryant | |
| 2013/0093149 A1 | 4/2013 | Saur et al. | |
| 2013/0098966 A1 | 4/2013 | Kostrzewski et al. | |
| 2013/0098968 A1 | 4/2013 | Aranyi et al. | |
| 2013/0098969 A1 | 4/2013 | Scirica et al. | |
| 2013/0105189 A1* | 5/2013 | Murthy | B25B 21/00 173/178 |
| 2013/0168431 A1* | 7/2013 | Zemlok | A61B 17/07207 227/175.1 |
| 2013/0181035 A1 | 7/2013 | Milliman | |
| 2013/0184704 A1 | 7/2013 | Beardsley et al. | |
| 2013/0214025 A1 | 8/2013 | Zemlok et al. | |
| 2013/0240596 A1 | 9/2013 | Whitman | |
| 2013/0274722 A1 | 10/2013 | Kostrzewski et al. | |
| 2013/0282052 A1 | 10/2013 | Aranyi et al. | |
| 2013/0292451 A1 | 11/2013 | Viola et al. | |
| 2013/0313304 A1 | 11/2013 | Shelton, IV et al. | |
| 2013/0317486 A1 | 11/2013 | Nicholas et al. | |
| 2013/0319706 A1 | 12/2013 | Nicholas et al. | |
| 2013/0324978 A1 | 12/2013 | Nicholas et al. | |
| 2013/0324979 A1 | 12/2013 | Nicholas et al. | |
| 2013/0334281 A1 | 12/2013 | Williams | |
| 2014/0012236 A1 | 1/2014 | Williams et al. | |
| 2014/0012237 A1 | 1/2014 | Pribanic et al. | |
| 2014/0012289 A1 | 1/2014 | Snow et al. | |
| 2014/0025046 A1 | 1/2014 | Williams et al. | |
| 2014/0107697 A1* | 4/2014 | Patani | A61B 17/12 606/208 |
| 2014/0110455 A1 | 4/2014 | Ingmanson et al. | |
| 2014/0144970 A1 | 5/2014 | Aranyi et al. | |
| 2014/0207125 A1 | 7/2014 | Applegate et al. | |
| 2014/0207182 A1 | 7/2014 | Zergiebel et al. | |
| 2014/0207185 A1 | 7/2014 | Goble et al. | |
| 2014/0236173 A1 | 8/2014 | Scirica et al. | |
| 2014/0236174 A1 | 8/2014 | Williams et al. | |
| 2014/0275872 A1* | 9/2014 | Merritt | A61B 5/14551 600/322 |
| 2014/0276932 A1 | 9/2014 | Williams et al. | |
| 2014/0299647 A1 | 10/2014 | Scirica et al. | |
| 2014/0303668 A1 | 10/2014 | Nicholas et al. | |
| 2014/0358129 A1 | 12/2014 | Zergiebel et al. | |
| 2014/0361068 A1 | 12/2014 | Aranyi et al. | |
| 2014/0373652 A1 | 12/2014 | Zergiebel et al. | |
| 2015/0048144 A1 | 2/2015 | Whitman | |
| 2015/0076205 A1 | 3/2015 | Zergiebel | |
| 2015/0076206 A1* | 3/2015 | Sapre | A61B 17/068 227/175.2 |
| 2015/0080912 A1 | 3/2015 | Sapre | |
| 2015/0157321 A1 | 6/2015 | Zergiebel et al. | |
| 2015/0164502 A1 | 6/2015 | Richard et al. | |
| 2015/0272577 A1 | 10/2015 | Zemlok et al. | |
| 2015/0272583 A1* | 10/2015 | Leimbach | A61B 17/07207 227/180.1 |

(56) References Cited

U.S. PATENT DOCUMENTS

| | | |
|---|---|---|
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 101234033 A | 8/2008 |
| CN | 101856251 A | 10/2010 |
| CN | 102028509 A | 4/2011 |
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1759652 A2 | 3/2007 |
| EP | 1769754 A1 | 4/2007 |
| EP | 1772105 A1 | 4/2007 |
| EP | 1 813 203 A2 | 8/2007 |
| EP | 1813199 A1 | 8/2007 |
| EP | 1813211 A2 | 8/2007 |
| EP | 1908412 A2 | 4/2008 |
| EP | 1917929 A1 | 5/2008 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 1952769 A2 | 8/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2090247 A1 | 8/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2245994 A1 | 11/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2377472 A1 | 10/2011 |
| EP | 2462878 A1 | 6/2012 |
| EP | 2462880 A2 | 6/2012 |
| EP | 2491872 A1 | 8/2012 |
| EP | 2586382 A2 | 5/2013 |
| EP | 2606834 A2 | 6/2013 |
| EP | 2668910 A2 | 12/2013 |
| EP | 2676615 A2 | 12/2013 |
| EP | 2815705 A1 | 12/2014 |
| ES | 2333509 A1 | 2/2010 |
| FR | 2861574 A1 | 5/2005 |
| JP | H0347249 A | 2/1991 |
| JP | 08-038488 | 2/1996 |
| JP | 2005-125075 A | 5/2005 |
| JP | 2010253272 A | 11/2010 |
| JP | 2011078772 A | 4/2011 |
| JP | 2011224368 A | 11/2011 |
| KR | 20120022521 A | 3/2012 |
| WO | 99/15086 A1 | 4/1999 |
| WO | 2000/072760 A1 | 12/2000 |
| WO | 2000/072765 A1 | 12/2000 |
| WO | 2003/000138 A2 | 1/2003 |
| WO | 2003/026511 A1 | 4/2003 |
| WO | 2003/030743 A2 | 4/2003 |
| WO | 2003065916 A1 | 8/2003 |
| WO | 2003/077769 A1 | 9/2003 |
| WO | 2003090630 A2 | 11/2003 |
| WO | 2004/107989 A1 | 12/2004 |
| WO | 2006/042210 A2 | 4/2006 |
| WO | 2007016290 A2 | 2/2007 |
| WO | 2007/026354 A1 | 3/2007 |
| WO | 2007137304 A2 | 11/2007 |
| WO | 2008/131362 A2 | 10/2008 |
| WO | 2008/133956 A2 | 11/2008 |
| WO | 2009039506 A1 | 3/2009 |
| WO | 2007014355 A3 | 4/2009 |
| WO | 2009/132359 A2 | 10/2009 |
| WO | 2009/143092 A1 | 11/2009 |
| WO | 2009149234 A1 | 12/2009 |
| WO | 2011/108840 A2 | 9/2011 |
| WO | 2012040984 A1 | 4/2012 |

OTHER PUBLICATIONS

Extended European Search Report corresponding to International Application No. EP 15 15 1076.5 dated Apr. 22, 2015.

Japanese Office Action corresponding to International Application No. JP 2011-084092 dated Jan. 14, 2016.

Extended European Search Report corresponding to International Application No. EP 12 19 7970.2 dated Jan. 28, 2016.

Chinese Office Action corresponding to International Application No. CN 201210560638.1 dated Oct. 21, 2015.

European Office Action corresponding to International Application No. EP 14 15 9056.2 dated Oct. 26, 2015.

Australian Examination Report No. 1 corresponding to International Application No. AU 2015200153 dated Dec. 11, 2015.

Australian Examination Report No. 1 corresponding to International Application No. AU 2014204542 dated Jan. 7, 2016.

Chinese Office Action corresponding to International Application No. CN 201310125449.6 dated Feb. 3, 2016.

Extended European Search Report corresponding to International Application No. EP 15 19 0245.9 dated Jan. 28, 2016.

Extended European Search Report corresponding to International Application No. EP 15 16 7793.7 dated Apr. 5, 2016.

European Office Action corresponding to International Application No. EP 14 18 4882.0 dated Apr. 25, 2016.

Extended European Search Report corresponding to International Application No. EP 14 19 6704.2 dated Sep. 24, 2015.

International Search Report and Written Opinion corresponding to Int'l Appln. No. PCT/US2015/051837, dated Dec. 21, 2015.

Extended European Search Report corresponding to International Application No. EP 14 19 7563.1 dated Aug. 5, 2015.

Partial European Search Report corresponding to International Application No. EP 15 19 0643.5 dated Feb. 26, 2016.

Extended European Search Report corresponding to International Application No. EP 15 16 6899.3 dated Feb. 3, 2016.

Extended European Search Report corresponding to International Application No. EP 14 19 9783.3 dated Dec. 22, 2015.

Extended European Search Report corresponding to International Application No. EP 15 17 3807.7 dated Nov. 24, 2015.

Extended European Search Report corresponding to International Application No. EP 15 19 0760.7 dated Apr. 1, 2016.

Extended European Search Report corresponding to International Application No. EP 15 17 3803.6 dated Nov. 24, 2015.

Extended European Search Report corresponding to International Application No. EP 15 17 3804.4 dated Nov. 24, 2015.

(56) References Cited

OTHER PUBLICATIONS

Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
European Search Report No. 14185097.4 dated Jan. 27, 2015.
European Search Report No. 13189650.8 dated Sep. 10, 2014.
Australian Examination Report dated May 14, 2018 in corresponding Australian Patent Application No. 2014218361.
Japanese Office Action dated May 17, 2018 in corresponding Japanese Patent Application No. 2014-187528, together with English translation.
Chinese Office Action dated Jun. 20, 2018 in corresponding Chinese Patent Application No. 201410479971.9 with English translation.
Australian Examination Report dated Apr. 26, 2018 in corresponding Australian Patent Application No. 2014218366.

* cited by examiner

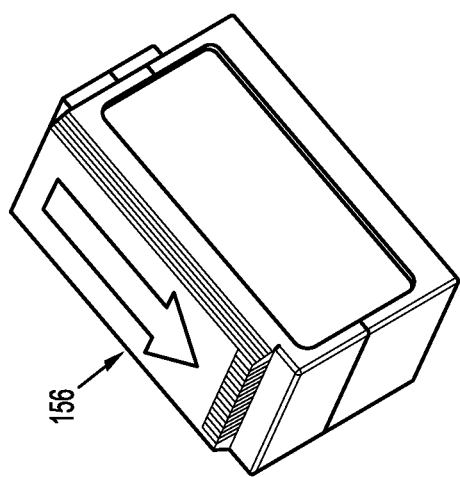
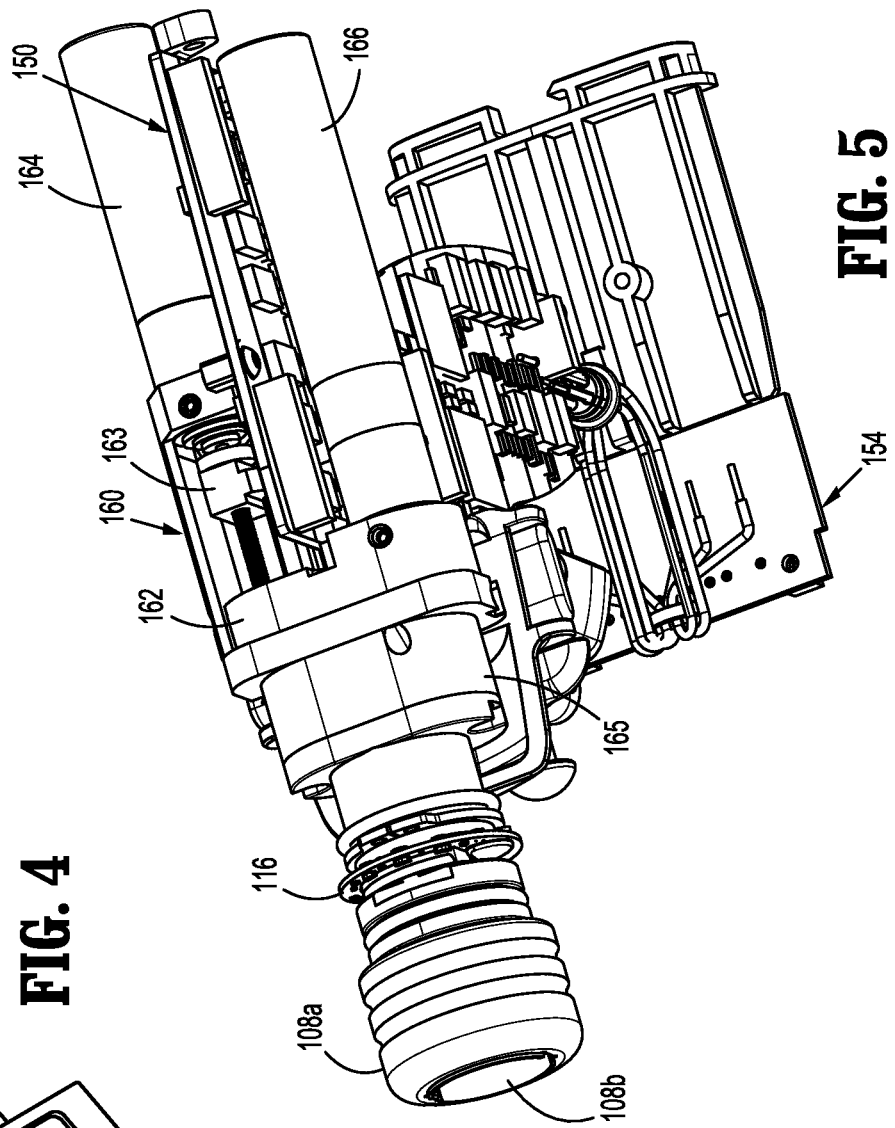
FIG. 4
FIG. 5

APPARATUS AND METHOD FOR DIFFERENTIATING BETWEEN TISSUE AND MECHANICAL OBSTRUCTION IN A SURGICAL INSTRUMENT

CROSS-REFERENCE TO RELATED APPLICATION

The present application claims the benefit of and priority to a U.S. Provisional Patent Application Ser. No. 61/879,445, filed on Sep. 18, 2013, the entire contents of which are incorporated by reference herein.

BACKGROUND

1. Technical Field

The present disclosure relates to surgical apparatuses, devices and/or systems for performing endoscopic surgical procedures and methods of use thereof. More specifically, the present disclosure relates to electromechanical, hand-held surgical apparatus, devices and/or systems configured for use with removable disposable end effectors and/or single use end effectors for clamping, cutting and/or stapling tissue.

2. Background of the Related Art

A number of surgical device manufacturers have developed product lines with proprietary drive systems for operating and/or manipulating electromechanical surgical devices. In many instances the electromechanical surgical devices include a reusable handle assembly, and disposable or single use end effectors. The end effectors are selectively connected to the handle assembly prior to use and then disconnected from the handle assembly following use in order to be disposed of or in some instances sterilized for re-use.

Many of these electromechanical surgical devices include complex drive components that utilize a variety of user interfaces that accept user inputs (e.g., controls) for controlling the devices as well as provide feedback to the user. To prevent actuation of drive mechanisms beyond mechanical limits, various switches and sensors are used to detect operational state of the surgical devices. Inclusion of multiple switches and/or sensors in the devices as well as end effectors presents various problems. In addition, cost or other considerations prevent the use of such devices. Accordingly, there is a need for systems and apparatuses having safety mechanisms that can detect mechanical limits without relying on multiple mechanical limit sensors and/or switches disposed throughout the surgical device.

SUMMARY

According to one embodiment of the present disclosure a surgical instrument is provided. The surgical instrument includes: a handle assembly; a jaw assembly including a staple cartridge containing a plurality of staples and an anvil to form the plurality of staples upon firing; a drive assembly at least partially located within the handle and connected to the jaw assembly and the lockout mechanism; a motor disposed within the handle assembly and operatively coupled to the drive assembly; and a controller operatively coupled to the motor, the controller configured to control supply of electrical current to the motor and to monitor a current draw of the motor, wherein the controller is further configured to terminate the supply of electrical current to the motor in response to a rate of change of the current draw indicative of a mechanical limit of at least one of the jaw assembly, the drive assembly, or the motor.

According to one aspect of the above embodiment, the controller is further configured to determine if motor current is unstable by determining whether the rate of change of the current draw is outside a first range.

According to one aspect of the above embodiment, the controller is further configured to determine if motor current is stable by determining whether the rate of change of the current draw is within a second range, wherein the second range is within the first range.

According to one aspect of the above embodiment, the controller is further configured to store a stability counter of current draw samples within the second range.

According to one aspect of the above embodiment, the controller determines whether motor current is stable if the stability counter is above a predetermined stability threshold.

According to one aspect of the above embodiment, the controller is further configured to determine if the motor reached the mechanical limit by determining whether the motor current is stable and the rate of change of the current draw is within a third range.

According to one aspect of the above embodiment, the third range is within the first range and is higher than the second range.

According to one aspect of the above embodiment, the controller is further configured to store an event counter of current draw samples within the third range.

According to one aspect of the above embodiment, the controller determines whether the motor reached the mechanical limit if the event counter is above a predetermined event threshold.

According to another embodiment of the present disclosure a surgical instrument is provided. The surgical instrument includes: a handle assembly; a jaw assembly including a staple cartridge containing a plurality of staples and an anvil to form the plurality of staples upon firing; a drive assembly at least partially located within the handle and connected to the jaw assembly and the lockout mechanism; a motor disposed within the handle assembly and operatively coupled to the drive assembly; and a controller operatively coupled to the motor, the controller to determine whether the motor has reached a mechanical limit based on a rate of change of a current draw by the motor indicative of the mechanical limit.

According to one aspect of the above embodiment, the controller is further configured to determine whether motor current is unstable by determining whether the rate of change of the current draw is outside a first range.

According to one aspect of the above embodiment, the controller is further configured to determine whether motor current is stable by determining whether a plurality of samples of the rate of change of the current draw are within a second range.

According to one aspect of the above embodiment, the controller is further configured to store a stability counter of current draw samples within the second range.

According to one aspect of the above embodiment, the controller determines whether motor current is stable if the stability counter is above a predetermined stability threshold.

According to one aspect of the above embodiment, the controller is further configured to determine whether the motor reached the mechanical limit by determining whether the motor current is stable and a plurality of samples of the rate of change of the current draw are within a third range.

According to one aspect of the above embodiment, the second and third ranges are within the first range and the third range is higher than the second range.

According to one aspect of the above embodiment, the controller is further configured to store an event counter of current draw samples within the third range.

According to one aspect of the above embodiment, the controller determines whether the motor reached the mechanical limit if the event counter is above a predetermined event threshold.

According to a further embodiment of the present disclosure a method for controlling a surgical instrument is provided. The method includes: monitoring a current draw of a motor coupled to a drive assembly for actuating a jaw assembly; calculating a rate of change of the current draw; and determining whether the motor has reached a mechanical limit based on the rate of change of the current draw by the motor.

According to one aspect of the above embodiment, the method further includes determining whether the rate of change of the current draw is outside a first range to determine whether motor current is unstable.

According to one aspect of the above embodiment, the method further includes determining whether a plurality of samples of the rate of change of the current draw are within a second range to determine whether motor current is stable.

According to one aspect of the above embodiment, the method further includes: storing a stability counter of current draw samples within the second range; and determining whether motor current is stable if the stability counter is above a predetermined stability threshold.

According to one aspect of the above embodiment, the method further includes: whether the motor current is stable and a plurality of samples of the rate of change of the current draw are within a third range to determine whether the motor reached the mechanical limit by.

According to one aspect of the above embodiment, the second and third ranges are within the first range and the third range is higher than the second range.

According to one aspect of the above embodiment, the method further includes: storing an event counter of current draw samples within the third range; and determining whether the motor reached the mechanical limit if the event counter is above a predetermined event threshold.

DESCRIPTION OF THE DRAWINGS

Embodiments of the present disclosure are described herein with reference to the accompanying drawings, wherein:

FIG. 4 is a perspective view of a battery of the surgical instrument of FIG. 1, according to the present disclosure;

FIG. 5 is a top, partially-disassembled view of the surgical instrument of FIG. 1, according to the present disclosure;

DETAILED DESCRIPTION

A surgical system, in accordance with an embodiment of the present disclosure, is generally designated as 10, and is in the form of a powered hand held electromechanical instrument configured for selective attachment thereto of a plurality of different end effectors that are each configured for actuation and manipulation by the powered hand held electromechanical surgical instrument.

Figure 1:
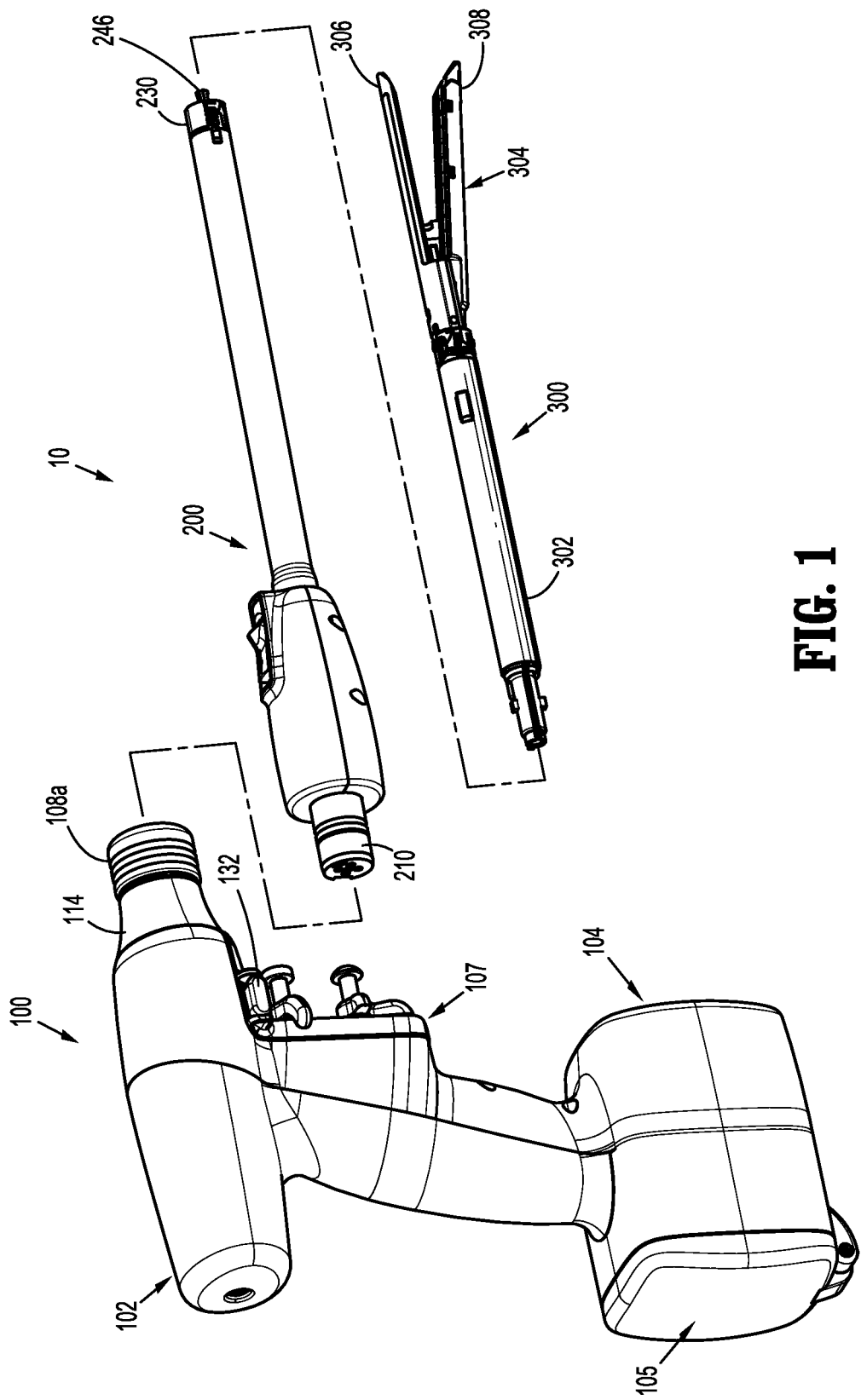
FIG. 1 is a perspective, disassembled view of an electromechanical surgical system including a surgical instrument, an adapter, and an end effector, according to the present disclosure.

As illustrated in FIG. 1, surgical instrument 100 is configured for selective connection with an adapter 200, and, in turn, adapter 200 is configured for selective connection with an end effector or single use loading unit 300.

Figure 2:
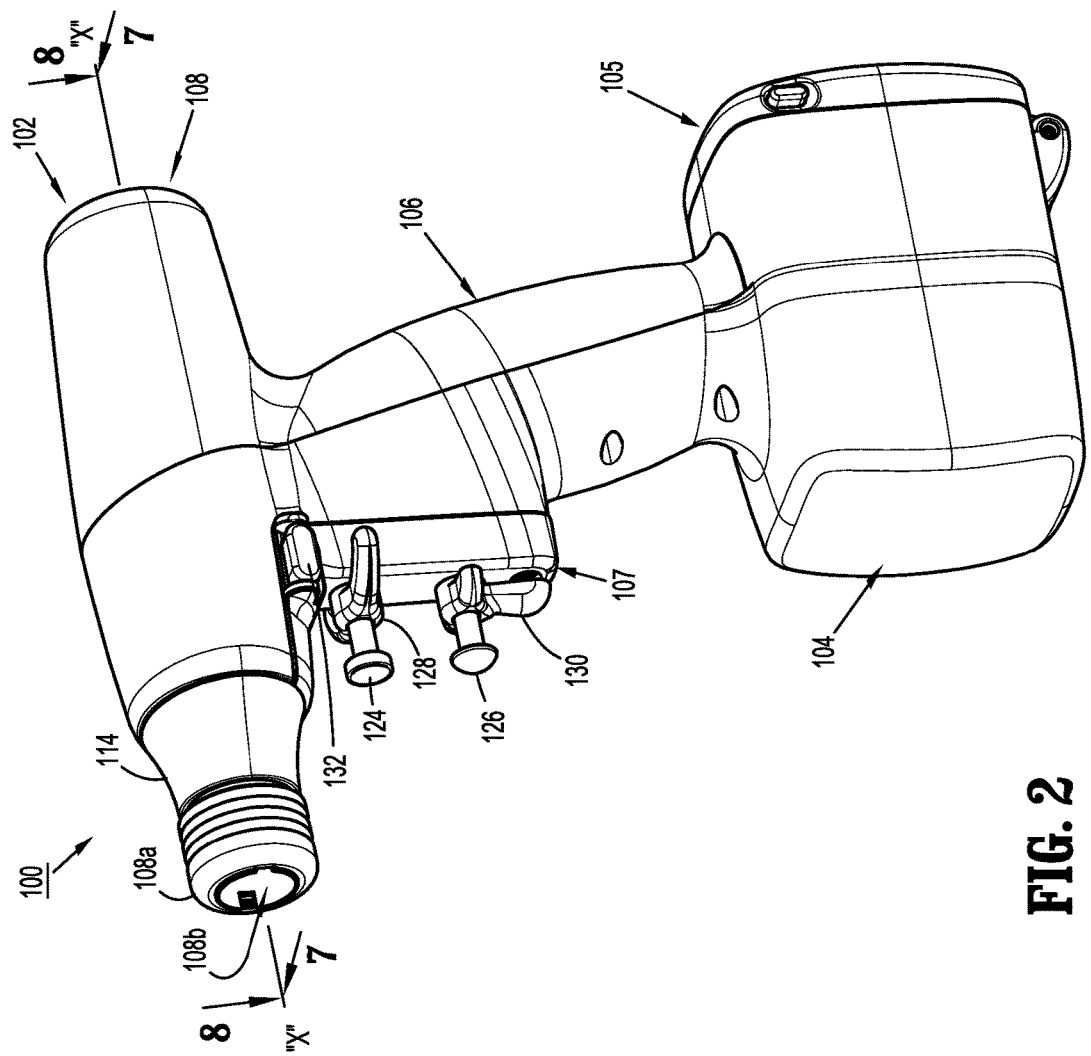
FIG. 2 is a perspective view of the surgical instrument of FIG. 1, according to the present disclosure.
Figure 3:
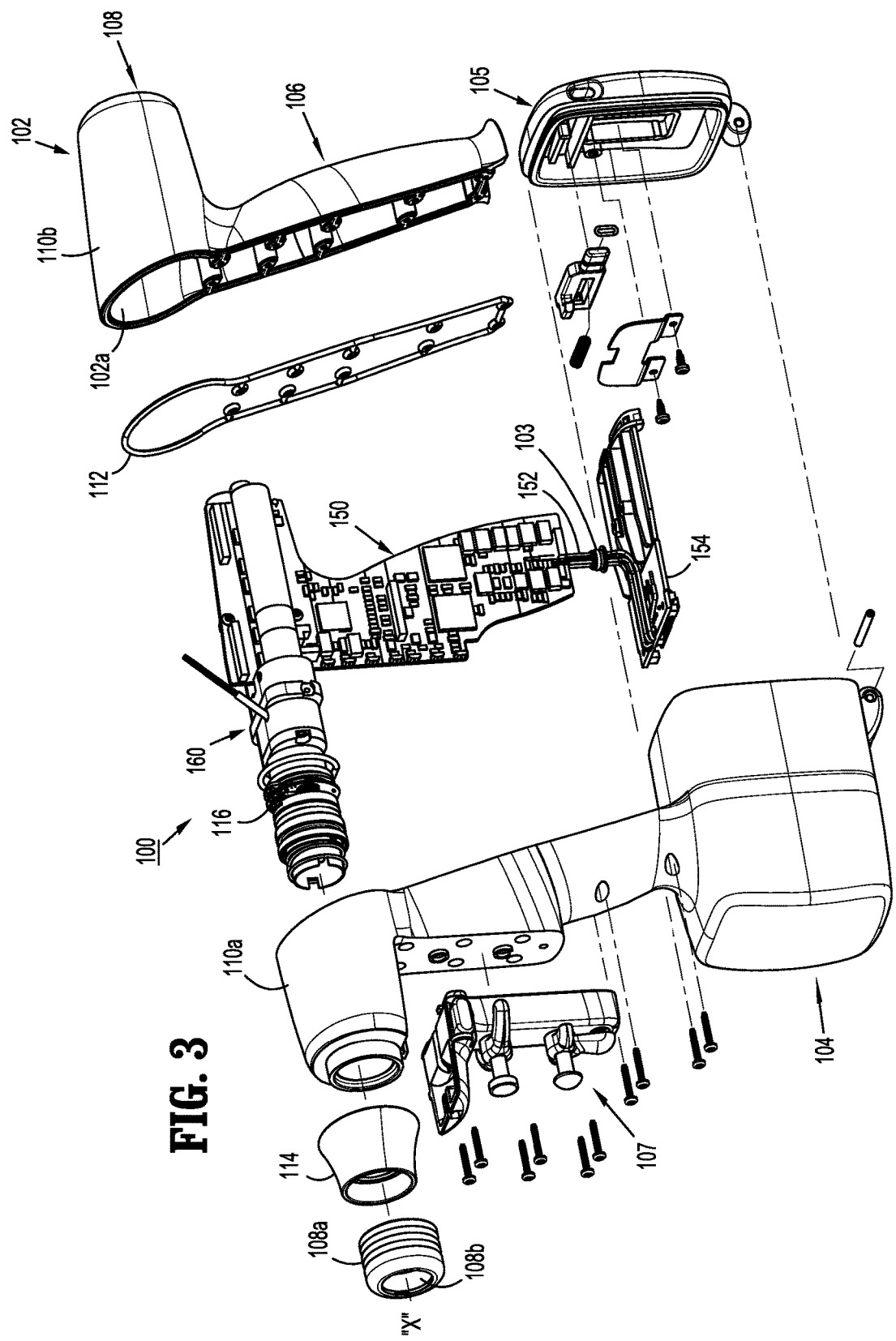
FIG. 3 is perspective, exploded view of the surgical instrument of FIG. 1, according to the present disclosure.

As illustrated in FIGS. 1-3, surgical instrument 100 includes a handle housing 102 having a lower housing portion 104, an intermediate housing portion 106 extending from and/or supported on lower housing portion 104, and an upper housing portion 108 extending from and/or supported on intermediate housing portion 106. Intermediate housing portion 106 and upper housing portion 108 are separated into a distal half-section 110a that is integrally formed with and extending from the lower portion 104, and a proximal half-section 110b connectable to distal half-section 110a by a plurality of fasteners. When joined, distal and proximal half-sections 110a, 110b define a handle housing 102 having a cavity 102a therein in which a circuit board 150 and a drive mechanism 160 is situated.

Distal and proximal half-sections 110a, 110b are divided along a plane that traverses a longitudinal axis "X" of upper housing portion 108, as seen in FIGS. 2 and 3. Handle housing 102 includes a gasket 112 extending completely around a rim of distal half-section and/or proximal half-section 110a, 110b and being interposed between distal half-section 110a and proximal half-section 110b. Gasket 112 seals the perimeter of distal half-section 110a and proximal half-section 110b. Gasket 112 functions to establish an air-tight seal between distal half-section 110a and proximal half-section 110b such that circuit board 150 and drive mechanism 160 are protected from sterilization and/or cleaning procedures.

In this manner, the cavity 102a of handle housing 102 is sealed along the perimeter of distal half-section 110a and proximal half-section 110b yet is configured to enable easier, more efficient assembly of circuit board 150 and a drive mechanism 160 in handle housing 102.

Intermediate housing portion 106 of handle housing 102 provides a housing in which circuit board 150 is situated. Circuit board 150 is configured to control the various operations of surgical instrument 100, as will be set forth in additional detail below.

Lower housing portion 104 of surgical instrument 100 defines an aperture (not shown) formed in an upper surface thereof and which is located beneath or within intermediate housing portion 106. The aperture of lower housing portion 104 provides a passage through which wires 152 pass to electrically interconnect electrical components (a battery 156, as illustrated in FIG. 4, a circuit board 154, as illustrated in FIG. 3, etc.) situated in lower housing portion 104 with electrical components (circuit board 150, drive mechanism 160, etc.) situated in intermediate housing portion 106 and/or upper housing portion 108.

Handle housing 102 includes a gasket 103 disposed within the aperture of lower housing portion 104 (not shown) thereby plugging or sealing the aperture of lower housing portion 104 while allowing wires 152 to pass therethrough. Gasket 103 functions to establish an air-tight seal between lower housing portion 106 and intermediate housing portion 108 such that circuit board 150 and drive mechanism 160 are protected from sterilization and/or cleaning procedures.

As shown, lower housing portion 104 of handle housing 102 provides a housing in which a rechargeable battery 156 is removably situated. Battery 156 is configured to supply power to any of the electrical components of surgical instrument 100. Lower housing portion 104 defines a cavity (not shown) into which battery 156 is inserted. Lower housing portion 104 includes a door 105 pivotally connected thereto for closing cavity of lower housing portion 104 and retaining battery 156 therein.

With reference to FIGS. 3 and 5, distal half-section 110a of upper housing portion 108 defines a nose or connecting portion 108a. A nose cone 114 is supported on nose portion 108a of upper housing portion 108. Nose cone 114 is fabricated from a transparent material. An illumination member 116 is disposed within nose cone 114 such that illumination member 116 is visible therethrough. Illumination member 116 is may be a light emitting diode printed circuit board (LED PCB). Illumination member 116 is configured to illuminate multiple colors with a specific color pattern being associated with a unique discrete event.

Upper housing portion 108 of handle housing 102 provides a housing in which drive mechanism 160 is situated. As illustrated in FIG. 5, drive mechanism 160 is configured to drive shafts and/or gear components in order to perform the various operations of surgical instrument 100. In particular, drive mechanism 160 is configured to drive shafts and/or gear components in order to selectively move tool assembly 304 of end effector 300 (see FIGS. 1 and 9) relative to proximal body portion 302 of end effector 300, to rotate end effector 300 about a longitudinal axis "X" (see FIG. 2) relative to handle housing 102, to move anvil assembly 306 relative to cartridge assembly 308 of end effector 300, and/or to fire a stapling and cutting cartridge within cartridge assembly 308 of end effector 300.

The drive mechanism 160 includes a selector gearbox assembly 162 that is located immediately proximal relative to adapter 200. Proximal to the selector gearbox assembly 162 is a function selection module 163 having a first motor 164 that functions to selectively move gear elements within the selector gearbox assembly 162 into engagement with an input drive component 165 having a second motor 166.

As illustrated in FIGS. 1-4, and as mentioned above, distal half-section 110a of upper housing portion 108 defines a connecting portion 108a configured to accept a corresponding drive coupling assembly 210 of adapter 200.

Figure 6:
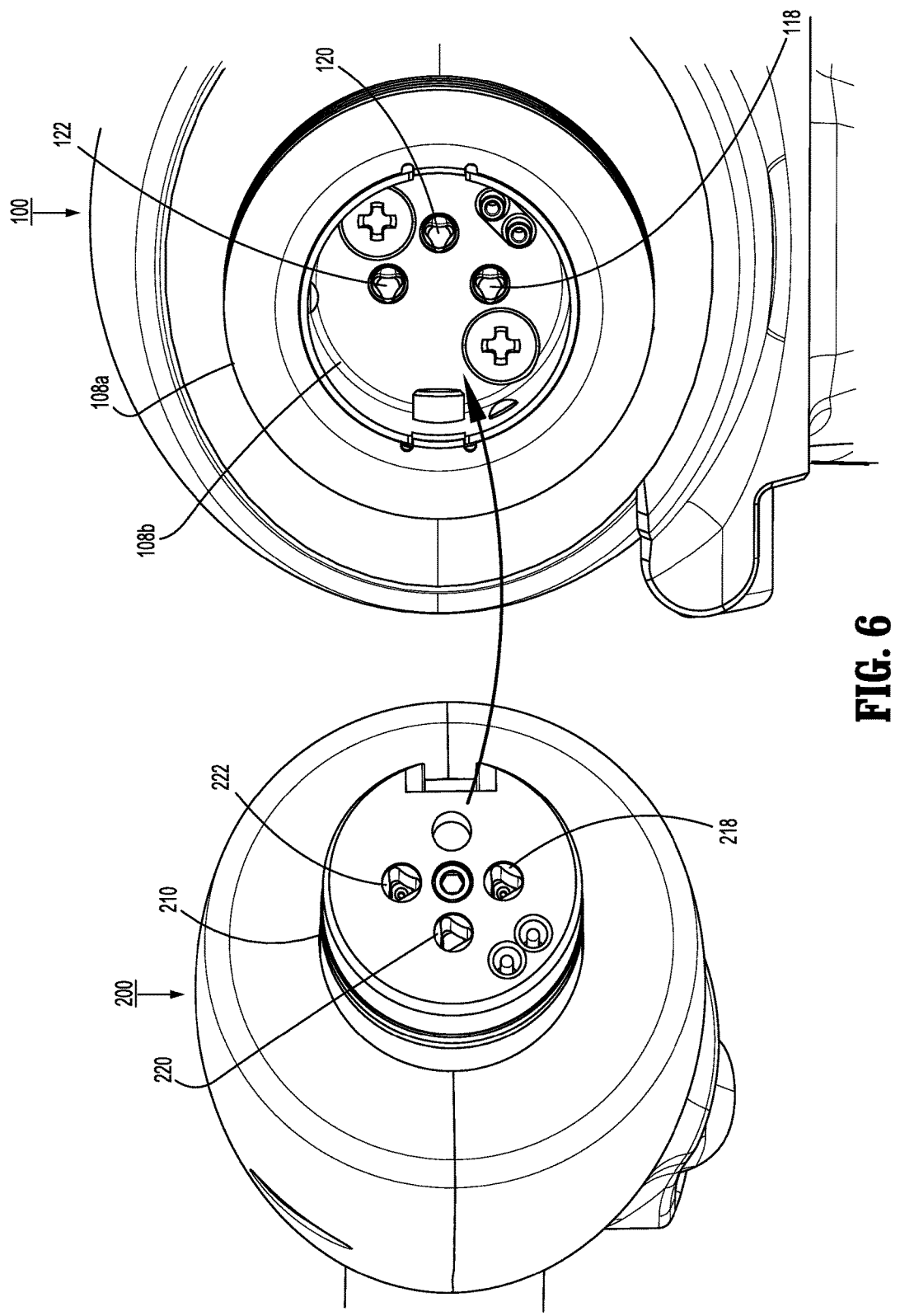
FIG. 6 is a front, perspective view of the surgical instrument of FIG. 1 with the adapter separated therefrom, according to the present disclosure.
Figure 7:
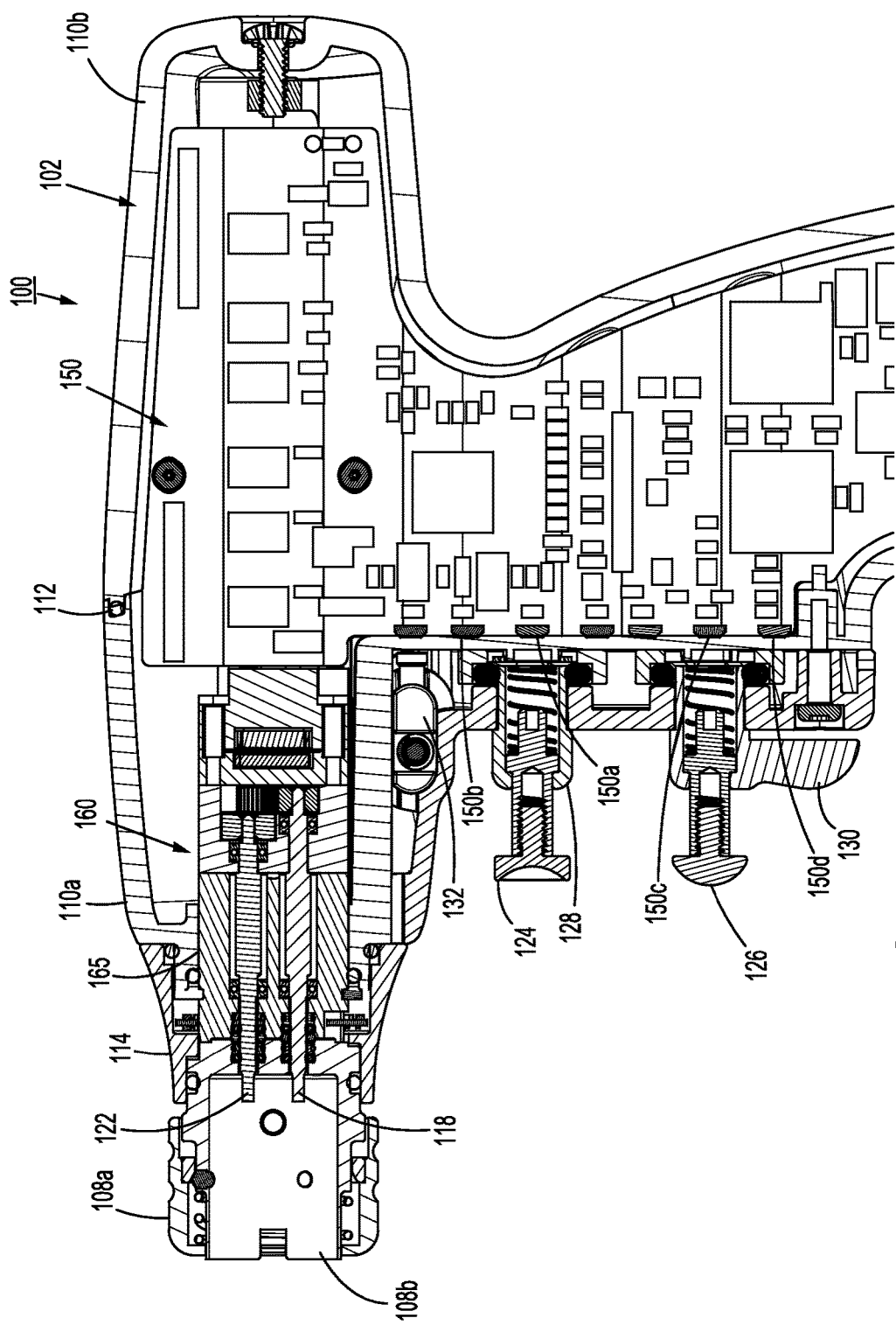
FIG. 7 is a side, cross-sectional view of the surgical instrument of FIG. 1, as taken through 7-7 of FIG. 2, according to the present disclosure.
Figure 8:
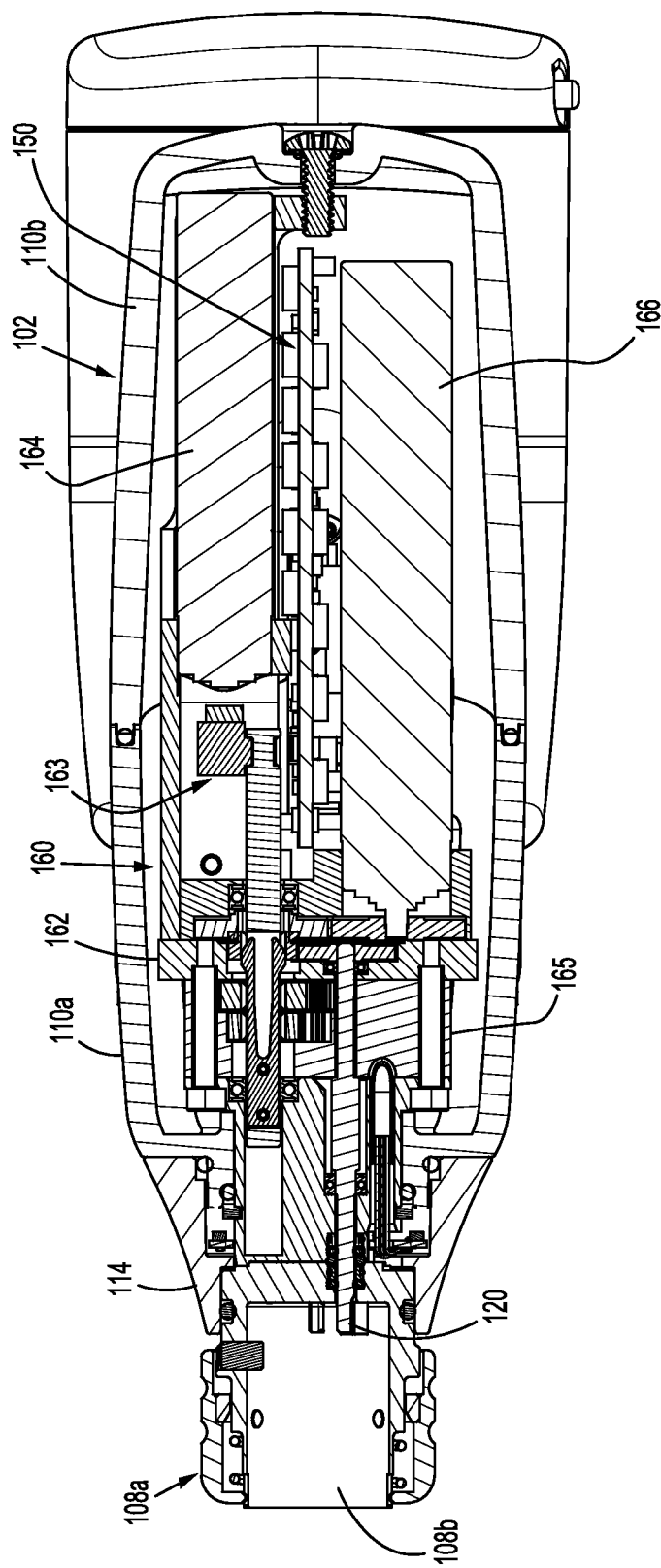
FIG. 8 is a top, cross-sectional view of the surgical instrument of FIG. 1, as taken through 8-8 of FIG. 2, according to the present disclosure.

As illustrated in FIGS. 6-8, connecting portion 108a of surgical instrument 100 has a cylindrical recess 108b that receives a drive coupling assembly 210 of adapter 200 when adapter 200 is mated to surgical instrument 100. Connecting portion 108a houses three rotatable drive connectors 118, 120, 122.

When adapter 200 is mated to surgical instrument 100, each of rotatable drive connectors 118, 120, 122 of surgical instrument 100 couples with a corresponding rotatable connector sleeve 218, 220, 222 of adapter 200 as shown in FIG. 6. In this regard, the interface between corresponding first drive connector 118 and first connector sleeve 218, the interface between corresponding second drive connector 120 and second connector sleeve 220, and the interface between corresponding third drive connector 122 and third connector sleeve 222 are keyed such that rotation of each of drive connectors 118, 120, 122 of surgical instrument 100 causes a corresponding rotation of the corresponding connector sleeve 218, 220, 222 of adapter 200.

The mating of drive connectors 118, 120, 122 of surgical instrument 100 with connector sleeves 218, 220, 222 of adapter 200 allows rotational forces to be independently transmitted via each of the three respective connector interfaces. The drive connectors 118, 120, 122 of surgical instrument 100 are configured to be independently rotated by drive mechanism 160. In this regard, the function selection module 163 of drive mechanism 160 selects which drive connector or connectors 118, 120, 122 of surgical instrument 100 is to be driven by the input drive component 165 of drive mechanism 160.

Since each of drive connectors 118, 120, 122 of surgical instrument 100 has a keyed and/or substantially non-rotatable interface with respective connector sleeves 218, 220, 222 of adapter 200, when adapter 200 is coupled to surgical instrument 100, rotational force(s) are selectively transferred from drive mechanism 160 of surgical instrument 100 to adapter 200.

The selective rotation of drive connector(s) 118, 120 and/or 122 of surgical instrument 100 allows surgical instrument 100 to selectively actuate different functions of end effector 300. As will be discussed in greater detail below, selective and independent rotation of first drive connector 118 of surgical instrument 100 corresponds to the selective and independent opening and closing of tool assembly 304 of end effector 300, and driving of a stapling/cutting component of tool assembly 304 of end effector 300. Also, the selective and independent rotation of second drive connector 120 of surgical instrument 100 corresponds to the selective and independent articulation of tool assembly 304 of end effector 300 transverse to longitudinal axis "X" (see FIG. 2). Additionally, the selective and independent rotation of third drive connector 122 of surgical instrument 100 corresponds to the selective and independent rotation of end effector 300 about longitudinal axis "X" (see FIG. 2) relative to handle housing 102 of surgical instrument 100.

As mentioned above and as illustrated in FIGS. 5 and 8, drive mechanism 160 includes a selector gearbox assembly 162; and a function selection module 163, located proximal to the selector gearbox assembly 162, that functions to selectively move gear elements within the selector gearbox assembly 162 into engagement with second motor 166.

Thus, drive mechanism 160 selectively drives one of drive connectors 118, 120, 122 of surgical instrument 100 at a given time.

As illustrated in FIGS. 1-3, handle housing 102 supports a control assembly 107 on a distal surface or side of intermediate housing portion 108. The control assembly 107 is a fully-functional mechanical subassembly that can be assembled and tested separately from the rest of the instrument 100 prior to coupling thereto.

Control assembly 107, in cooperation with intermediate housing portion 108, supports a pair of finger-actuated control buttons 124, 126 and a pair rocker devices 128, 130 within a housing 107a. The control buttons 124, 126 are coupled to extension shafts 125, 127 respectively. In particular, control assembly 107 defines an upper aperture 124a for slidably receiving the extension shaft 125, and a lower aperture 126a for slidably receiving the extension shaft 127.

Reference may be made to a commonly-owned U.S. patent application Ser. No. 13/331,047, the entire contents of which are incorporated by reference herein, for a detailed discussion of the construction and operation of the surgical instrument 100.

Figure 9:
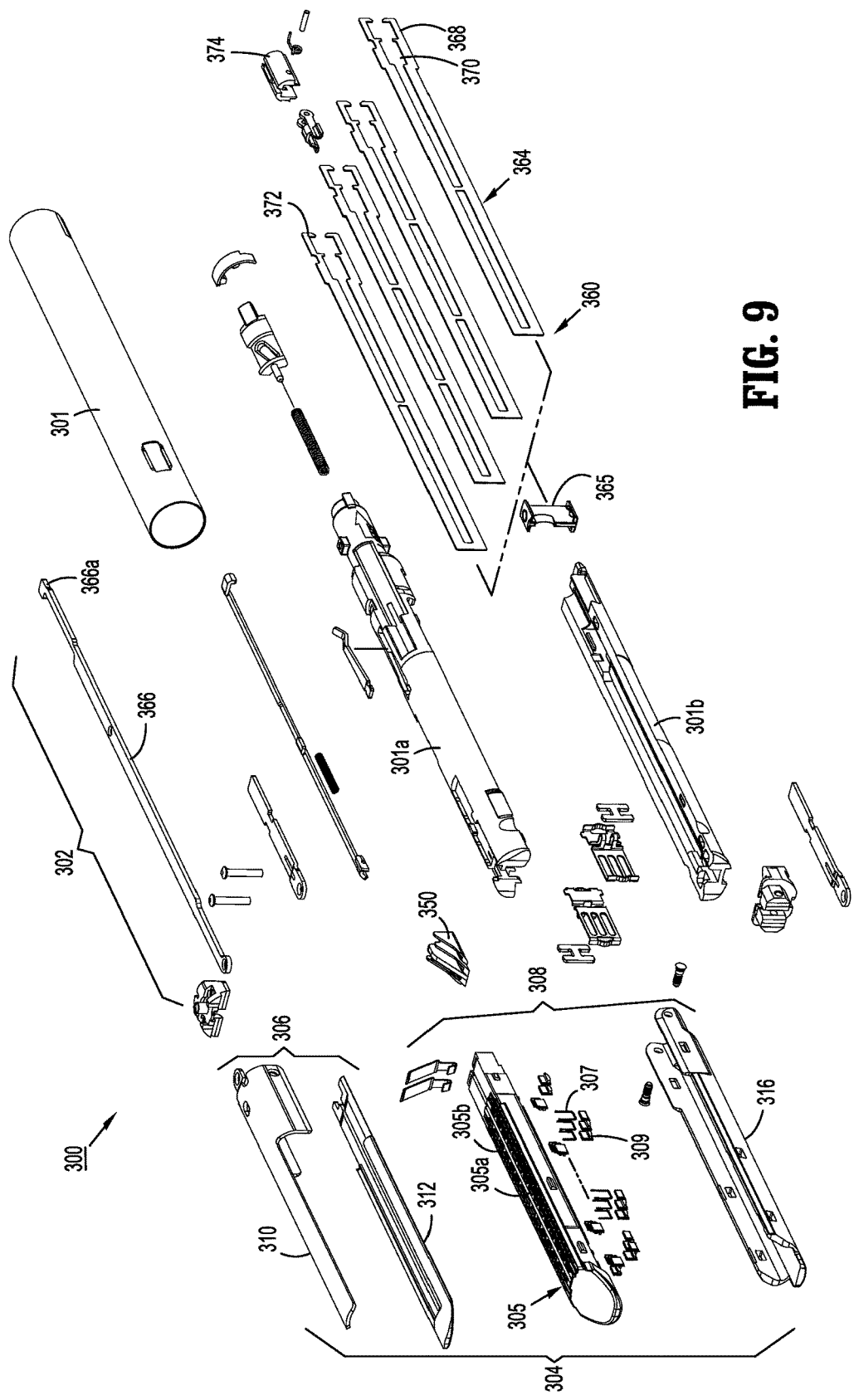
FIG. 9 is a perspective, exploded view of a end effector of FIG. 1, according to the present disclosure.

Referring to FIG. 9, drive assembly 360 of end effector 300 includes a flexible drive shaft 364 having a distal end which is secured to a dynamic drive beam 365, and a proximal engagement section 368. Engagement section 368 includes a stepped portion defining a shoulder 370. A proximal end of engagement section 368 includes diametrically opposed inwardly extending fingers 372. Fingers 372 engage a hollow drive member 374 to fixedly secure drive member 374 to the proximal end of shaft 364. Drive member 374 defines a proximal porthole which receives a connection member of drive tube 246 (FIG. 1) of adapter 200 when end effector 300 is attached to distal coupling 230 of adapter 200.

When drive assembly 360 is advanced distally within tool assembly 304, an upper beam of drive beam 365 moves within a channel defined between anvil plate 312 and anvil cover 310 and a lower beam moves within a channel of the staple cartridge 305 and over the exterior surface of carrier 316 to close tool assembly 304 and fire staples therefrom.

Proximal body portion 302 of end effector 300 includes a sheath or outer tube 301 enclosing an upper housing portion 301a and a lower housing portion 301b. The housing portions 301a and 301b enclose an articulation link 366 having a hooked proximal end 366a which extends from a proximal end of end effector 300. Hooked proximal end 366a of articulation link 366 engages a coupling hook (not shown) of adapter 200 when end effector 300 is secured to distal housing 232 of adapter 200. When drive bar (not shown) of adapter 200 is advanced or retracted as described above, articulation link 366 of end effector 300 is advanced or retracted within end effector 300 to pivot tool assembly 304 in relation to a distal end of proximal body portion 302.

As illustrated in FIG. 9 above, cartridge assembly 308 of tool assembly 304 includes a staple cartridge 305 supportable in carrier 316. Staple cartridge 305 defines a central longitudinal slot 305a, and three linear rows of staple retention slots 305b positioned on each side of longitudinal slot 305a. Each of staple retention slots 305b receives a single staple 307 and a portion of a staple pusher 309. During operation of instrument 100, drive assembly 360 abuts an actuation sled 350 and pushes actuation sled 350 through cartridge 305. As the actuation sled moves through cartridge 305, cam wedges of the actuation sled 350 sequentially engage staple pushers 309 to move staple pushers 309 vertically within staple retention slots 305b and sequentially eject a single staple 307 therefrom for formation against anvil plate 312.

The end effector 300 may also include one or more mechanical lockout mechanisms, such as those described in commonly-owned U.S. Pat. Nos. 5,071,052, 5,397,046, 5,413,267, 5,415,335, 5,715,988, 5,718,359, 6,109,500, the entire contents of all of which are incorporated by reference herein.

Figure 10:
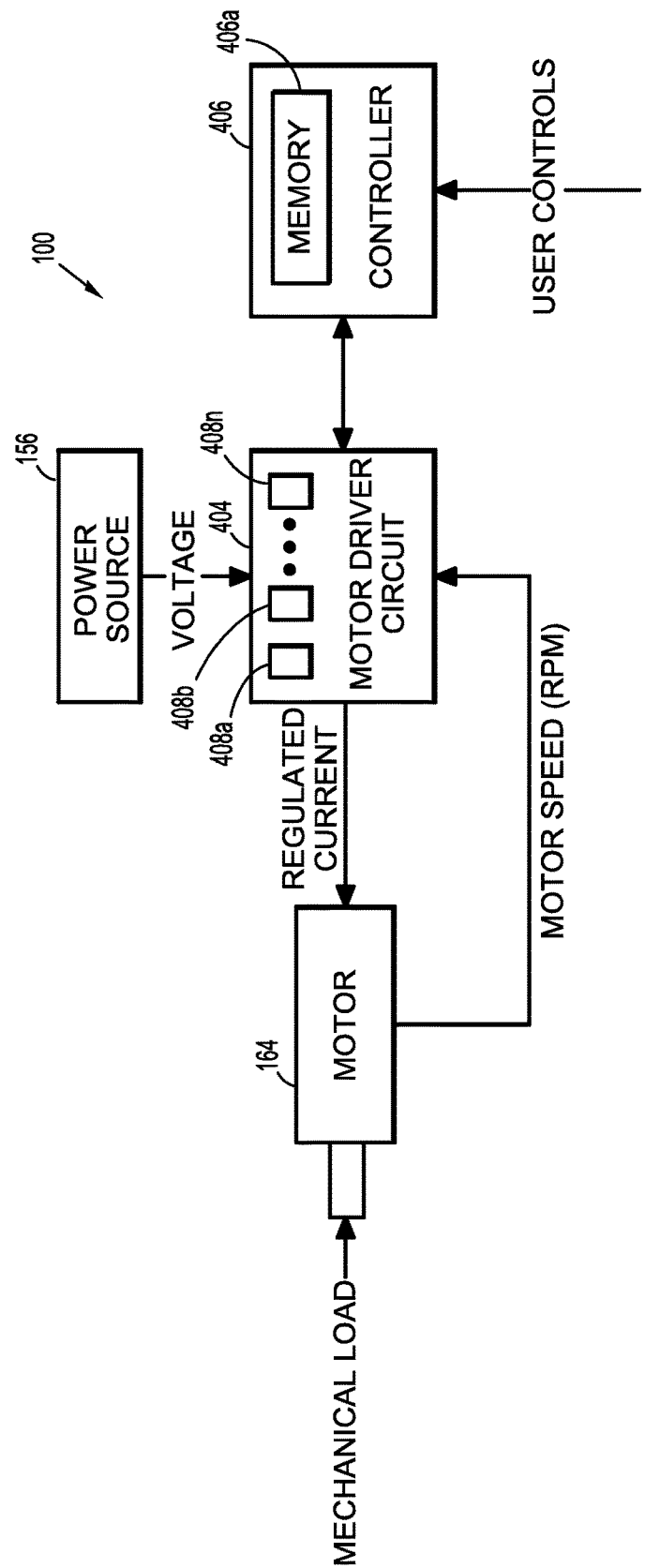
FIG. 10 is a schematic diagram of the surgical instrument of FIG. 1 according to the present disclosure.

Another embodiment of the instrument 100 is shown in FIG. 10. The instrument 100 includes the motor 164. The motor 164 may be any electrical motor configured to actuate one or more drives (e.g., rotatable drive connectors 118, 120, 122 of FIG. 6). The motor 164 is coupled to the battery 156, which may be a DC battery (e.g., rechargeable lead-based, nickel-based, lithium-ion based, battery etc.), an AC/DC transformer, or any other power source suitable for providing electrical energy to the motor 164.

The battery 156 and the motor 164 are coupled to a motor driver circuit 404 disposed on the circuit board 154 which controls the operation of the motor 164 including the flow of electrical energy from the battery 156 to the motor 164. The driver circuit 404 includes a plurality of sensors 408a, 408b, . . . 408n configured to measure operational states of the motor 164 and the battery 156. The sensors 408a-n may include voltage sensors, current sensors, temperature sensors, telemetry sensors, optical sensors, and combinations thereof. The sensors 408a-408n may measure voltage, current, and other electrical properties of the electrical energy supplied by the battery 156. The sensors 408a-408n may also measure rotational speed as revolutions per minute (RPM), torque, temperature, current draw, and other operational properties of the motor 164. RPM may be determined by measuring the rotation of the motor 164. Position of various drive shafts (e.g., rotatable drive connectors 118, 120, 122 of FIG. 6) may be determined by using various linear sensors disposed in or in proximity to the shafts or extrapolated from the RPM measurements. In embodiments, torque may be calculated based on the regulated current draw of the motor 164 at a constant RPM. In further embodiments, the driver circuit 404 and/or the controller 406 may measure time and process the above-described values as a function thereof, including integration and/or differentiation, e.g., to determine the change in the measured values and the like.

The driver circuit 404 is also coupled to a controller 406, which may be any suitable logic control circuit adapted to perform the calculations and/or operate according to a set of instructions described in further detail below. The controller 406 may include a central processing unit operably connected to a memory which may include transitory type memory (e.g., RAM) and/or non-transitory type memory (e.g., flash media, disk media, etc.). The controller 406 includes a plurality of inputs and outputs for interfacing with the driver circuit 404. In particular, the controller 406 receives measured sensor signals from the driver circuit 404 regarding operational status of the motor 164 and the battery 156 and, in turn, outputs control signals to the driver circuit 404 to control the operation of the motor 164 based on the sensor readings and specific algorithm instructions, which are discussed in more detail below. The controller 406 is also configured to accept a plurality of user inputs from a user interface (e.g., switches, buttons, touch screen, etc. of the control assembly 107 coupled to the controller 406).

The present disclosure provides for an apparatus and method for controlling the instrument 100 or any other powered surgical instrument, including, but not limited to, linear powered staplers, circular or arcuate powered staplers, graspers, electrosurgical sealing forceps, rotary tissue blending devices, and the like. In particular, torque, RPM, position, and acceleration of drive shafts of the instrument 100 can be correlated to motor characteristics (e.g., current draw). Current drawn by the motor 164 may be used for detecting mechanical limits since the current drawn by the motor 164 changes with the load and speed of the motor 164. Thus, analysis of the amount of change (e.g., rate of change) of current draw allows for distinguishing between different types of load conditions, e.g., load exerted by tissue versus load exerted by a mechanical stop.

During normal operation of the motor 164 the current draw generally does not fall outside a predetermined range (e.g., first range). During clamping and stapling, the load exerted on the motor 164 by the tissue varies within a second range, encompassed by the first range. In particular, as the motor 164 encounters an increased load due to the tissue being clamped by the anvil and cartridge assemblies 306, 308 the current draw increases and is within the second range for a second period of time (e.g., increase in the current draw occurs for a predetermined period of time). If the motor 164 encounters a mechanical limit there is also a corresponding increase in current draw in a relatively short time that is larger than the current draw associated with tissue clamping. In particular, the current draw due to a mechanical stop is within a third range that is higher than the second range for a third period of time. In comparison, startup of the motor 164 draws more current than either clamping/fastening or the mechanical stop and the duration of the increased current draw is the shortest of the two current draws described above.

In embodiments, mechanical stops may be detected by comparing motor current with a predetermined threshold since the current drawn by the motor 164 upon encountering a mechanical stop is usually much higher than the normal operating current. The controller 406 may use the satisfaction of this condition to shut off the motor 164.

This approach presents some challenges when the motor 164 encounters high momentary loads during normal operation (e.g., clamping tissue). The current draw associated with tissue clamping can reach the threshold, thus causing the controller 406 to shut off the motor 164 prematurely. In embodiments, the premature shutoff may be prevented by analyzing normal current draw of the motor 164 and construct a normal motor load profile. The controller 406 may then be programmed to adjust the shutoff threshold in accordance with that profile. This configuration is well-suited to motors 164 having little variation in the load profile. However, large variations can produce false positives if the load profile deviates from the current draw associated with normal use.

Efficiency of the motor 164 and drive mechanism also have an effect in calculating the motor current limit. Since mechanical efficiencies can vary from one instrument to another, each instrument needs to be individually calibrated during assembly. Further, mechanical efficiencies change with wear and tear of the instrument and can also affect performance of the software.

The algorithm according to the present disclosure overcomes the issues of using single-threshold or profile-based algorithms. An advantage of the algorithm according to the present disclosure is that the algorithm utilizes rate of change/current over time rather than comparing amplitude of the motor current to a predetermined threshold. The rate of change of the motor current associated with different loads, e.g., normal load, heavy loads, mechanical stops, load spikes, etc. may be classified into different ranges, in which each range is associated with a specific load. The classification into ranges may then be used to identify distinct loads on the motor 164 and filtering out spikes caused by starting and stopping of the motor 164. Since the identification of the mechanical loads is based on the rate of change in motor current rather than its amplitude, deviation from the load profiles do not affect load identification. In addition, mechanical efficiencies do not affect load identification based on rate of change in motor current. Less efficient instruments draw more current to attain the same speed, however, the slopes (e.g., rate of change in current draw) for reaching those speeds remains similar to those of more efficient systems. This eliminates the need for load profiling and calibration operation during assembly of the instrument 100.

Another advantage of the algorithm according to the present disclosure is the low computational overhead. The algorithm relies on calculating the rate of change of the motor current and as such can be determined by taking the difference between two values, allowing for implementation of the algorithm in an 8-bit microcontroller.

The change in motor current can be measured by sampling current periodically. In embodiments, the sampling rate may be from about 100 per second to about 10,000 per second, in embodiments from about 500 per second to about 1,000 per second. The samples may then be used by the controller 406 to calculate the change in the motor current (e.g., current draw). The controller 406 may then use the change in motor current to determine the operating condition of the instrument 100 and take appropriate action.

The present disclosure also provides a feedback system and method for controlling the instrument 100 based on external operating conditions such as firing difficulty encountered by the instrument 100 due to tissue thickness and/or mechanical stop (e.g., the drive beam 365 reaching the distal end of the channel defined in the anvil plate 312 and the staple cartridge 305. In addition, the present disclosure provides for modeling of different usages of the instrument 100 in response to the external operating conditions (e.g., specific failures) to derive internal system feedback. The sensor information from the sensors 408a-n is used by the controller 406 to alter operating characteristics of the instrument 100 and/or notify users of specific operational conditions. In embodiments, the controller 406 controls (e.g., limits) the current supplied to the motor 164.

The controller 406 includes a computer-readable memory 406a and/or non-transitory medium for storing software instructions (e.g., algorithm) for detecting mechanical limits of the instrument 100 based on the measured current draw. As used herein, the term "mechanical limit" denotes any of the electromechanical components reaching end-of-travel positions including, but not limited to, e.g., the drive beam 365 reaching the distal end of the channel defined in the anvil plate 312 and the staple cartridge 305, actuation of mechanical safety lockout mechanisms preventing travel of the shaft 364, articulation link 366 reaching articulation limits of the end effector 300, and the like.

The change in motor current associated with the onset of certain load conditions (e.g., tissue clamping or mechanical limits) falls within predefined ranges and persists for a certain duration. These conditions are used by the algorithm to identify operating properties of the motor 164 and react accordingly in response thereto.

Figure 11:
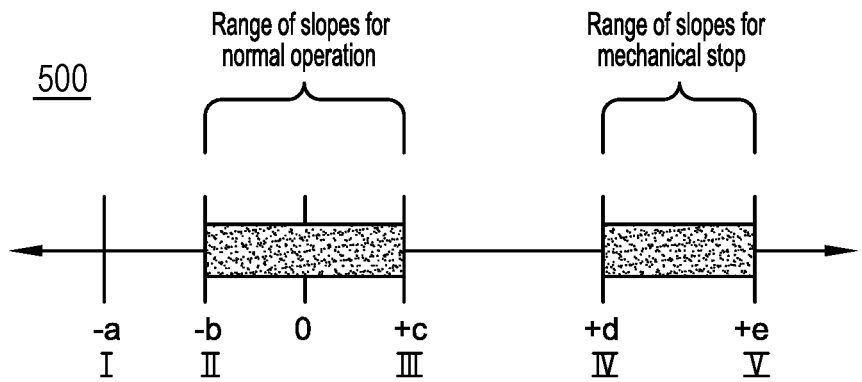
FIG. 11 is a schematic diagram of motor current values stored in memory of the surgical instrument of FIG. 1 according to the present disclosure.

With reference to FIG. 11, the memory 406a stores a plurality of current draw values. The memory 406a includes look-up table 500 or any other suitable data structure having values "I-V." The first value I and the fifth value "V" define a first range encompassing a stable current draw signal indicative of normal (e.g., load-bearing) operation of the motor 164. The second and third values "II" and "III" define a second range corresponding to the current draw associated with current draw of the motor 164 during tissue clamping and fourth and fifth values "IV" and "V" defining a third range corresponding to the current draw associated with a mechanical stop. In embodiments, the first value "I" may be the same as the second value "II."

The controller 406 also includes a condition-of-interest counter which counts the number of samples during which the slope (e.g., rate of change) of the motor current lies within the desired range (e.g., either first, second or third ranges). The controller 406 also includes a signal stability counter, which counts the number of samples for which the slope lies within the second range. The controller 406 determines if the measured rate of change current draw signal is stable using the values of the table 500. The signal is considered to be unstable if a predetermined number of current draw samples are outside the first range and stable if a predetermined number of samples are within the second range.

Figure 12:
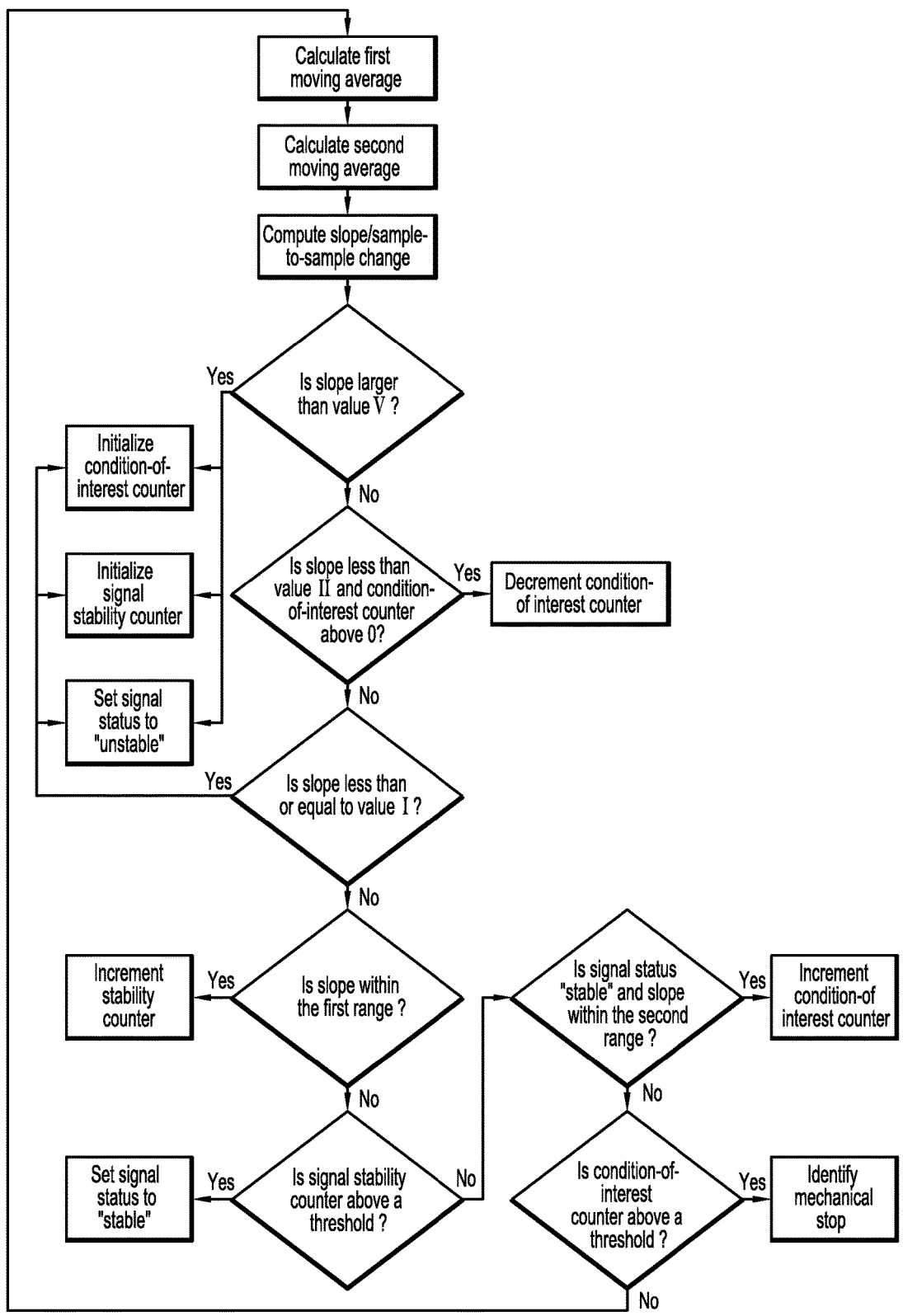
FIG. 12 is a flow chart of a method for controlling the surgical instrument of FIG. 1 according to the present disclosure.

FIG. 12 shows a method according to the present disclosure for determining if the motor 164 encounters a mechanical stop. The method may be implemented as software instructions (e.g., algorithm) stored in the controller 406 as described above. Initially, the controller 406 calculates a moving average of the measured motor current (e.g., current draw). As used herein, the term "moving average" denotes an average of a predetermined subset of samples that is updated every time a new sample is obtained. The moving average may include from about 2 plurality of samples to about 256 plurality of samples, and in embodiments, from about plurality of samples 16 about plurality of samples 64, depending on the sampling rate described above. The controller 406 stores the first moving average and calculates the second moving average for the subsequent sample set. The controller 406 then determines the difference between the moving averages to calculate the sample-to-sample change.

Figure 13:
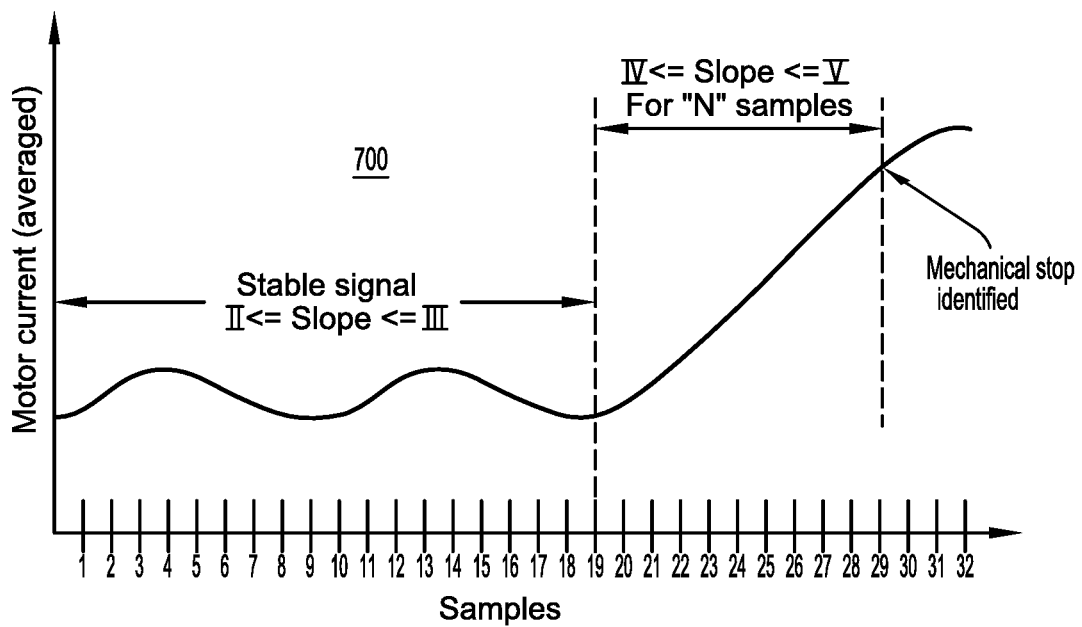
FIGS. 13-15 are plots of motor current of the surgical instrument as controlled by the method of the present disclosure.

As shown in FIGS. 12-13, the moving average of the samples may be graphed as plots 700, 800, 900, with the sample-to-sample change being represented as the slope of the plots 700, 800, 900. The plots 700, 800, 900 may be generated and outputted on a display allowing the user to view the current draw of the motor 164. In embodiments, the plots 700, 800, 900 may be stored in the memory 406a as a series of values, without reproducing the sample values as a plot.

The change in the monitored motor current, also defined as the slope is used to differentiate between different types of loads encountered by motor 164. The controller 406 initially determines if the signal is stable by determining whether the calculated slope/change is outside the first range (e.g., the slope is larger than fifth value "V" or less than first value "I"). If the slope lies outside the first range for a predefined number of samples, the controller 406 initializes or resets the condition-of-interest and signal stability counters by setting them to zero, 0. In addition, the controller 406 also sets the signal status as "unstable."

Figure 14:
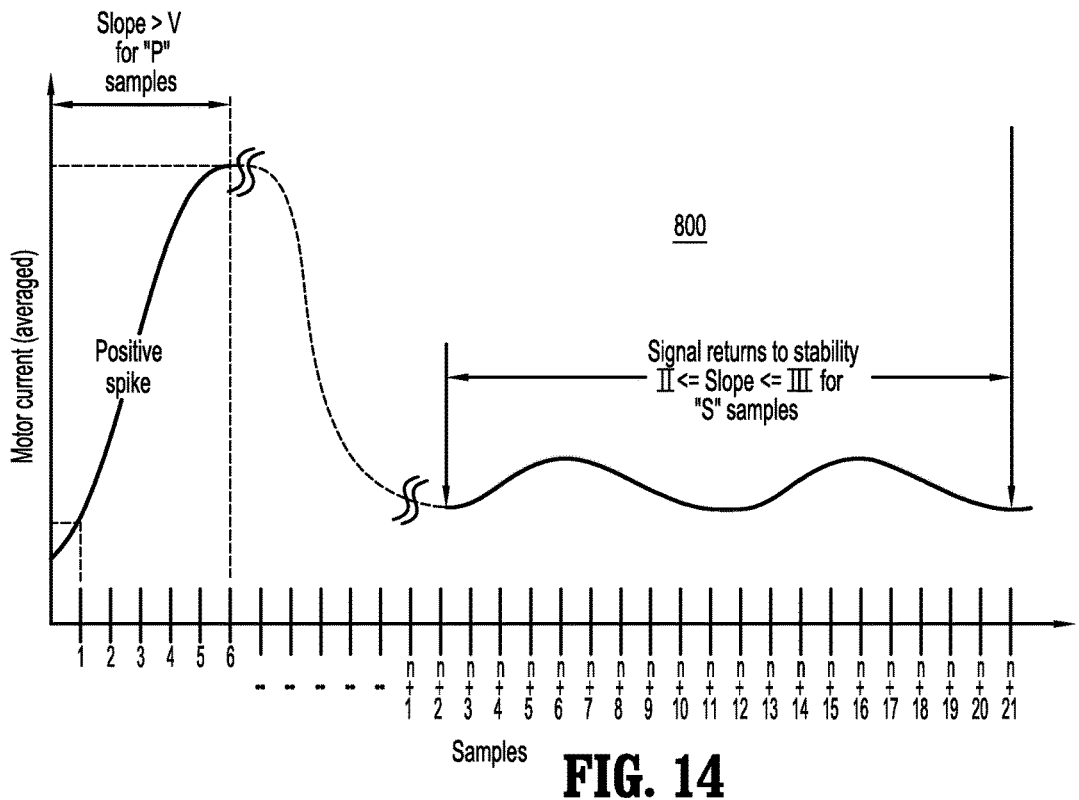
Figure 15:
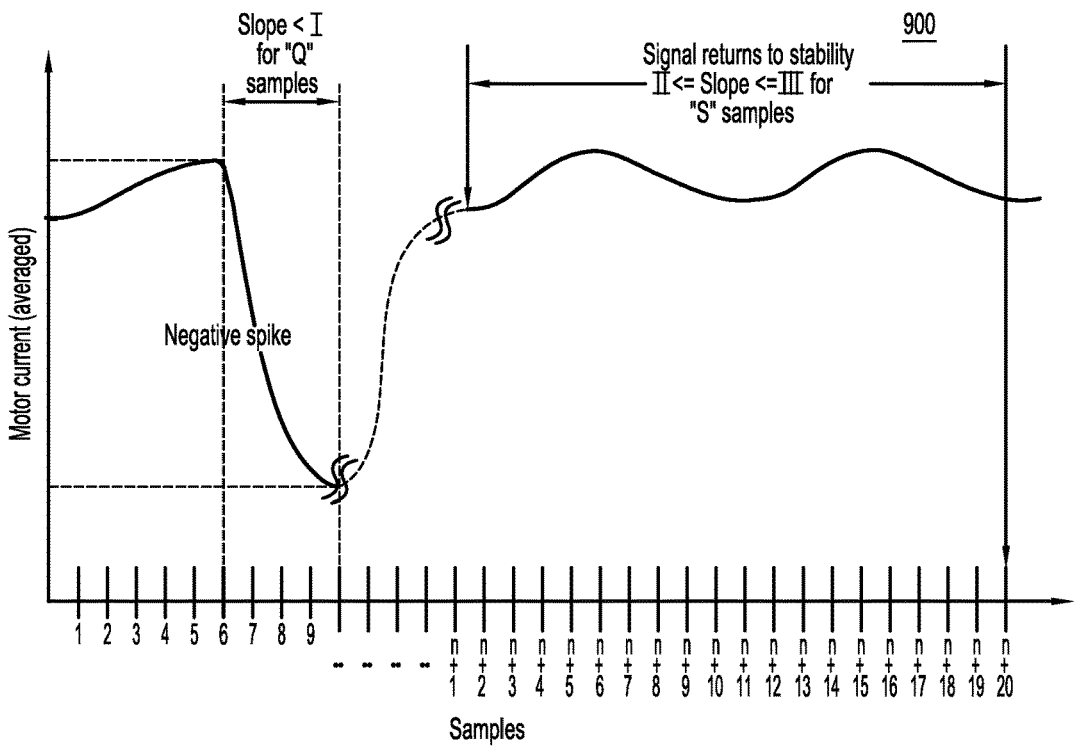

With reference to FIGS. 14 and 15, the samples below first value "I," as shown in FIG. 14, and above the fifth value "V," as shown in FIG. 15, are filtered out since they represent abnormal negative and positive spikes in current draw. These spikes may be caused by starting and stopping of the motor 164 and may result false positives in threshold-based decision making algorithms.

After determining if the slope is outside the first range, the controller 406 determines if the slope is within the second range (value II≤slope≤value III). If so, the stability counter is incremented. The controller 406 checks if the stability counter has reached a predetermined threshold before changing the signal status to "stable." This ensures that the sample has been within the second range for a sufficient period of time. Any deviation, e.g., the slope being outside the first range, resets the condition-of-interest and signal stability counters and sets the signal status as "unstable" as described above.

With reference to FIGS. 13-15, the signal is considered to be stable if the slope is within the second range, irrelevant of the actual amplitude of the motor current samples. Thus, the higher amplitude of the samples within the second range of FIG. 15 and lower amplitude of the samples within the second range of FIGS. 13 and 14 is treated similarly by the algorithm of the present disclosure as the attribute of interest is the rate of change of slope of the motor current samples.

The controller 406 also determines if the sample is within the third range. For each sample within the third range, while the signal is deemed stable, the condition-of-interest counter is incremented. Every time the sample falls below second value "II," the condition-of-interest counter is decremented. The condition-of-interest counter is used to identify a mechanical stop, as described in further detail below. If the condition-of-interest counter is above a predetermined threshold, then the controller 406 determines that a mechanical stop has been reached. With reference to FIG. 13, a plurality of samples have a slope that falls within the third range, this increments the condition-of-interest counter and upon reaching the predetermined count triggers the indication that the mechanical stop has been reached. Once the controller 406 determines that the mechanical limit has been reached the supply of current to the motor 164 may be terminated to prevent further operation of the instrument 100 and/or the instrument 100 may issue an alarm.

Figure 16:
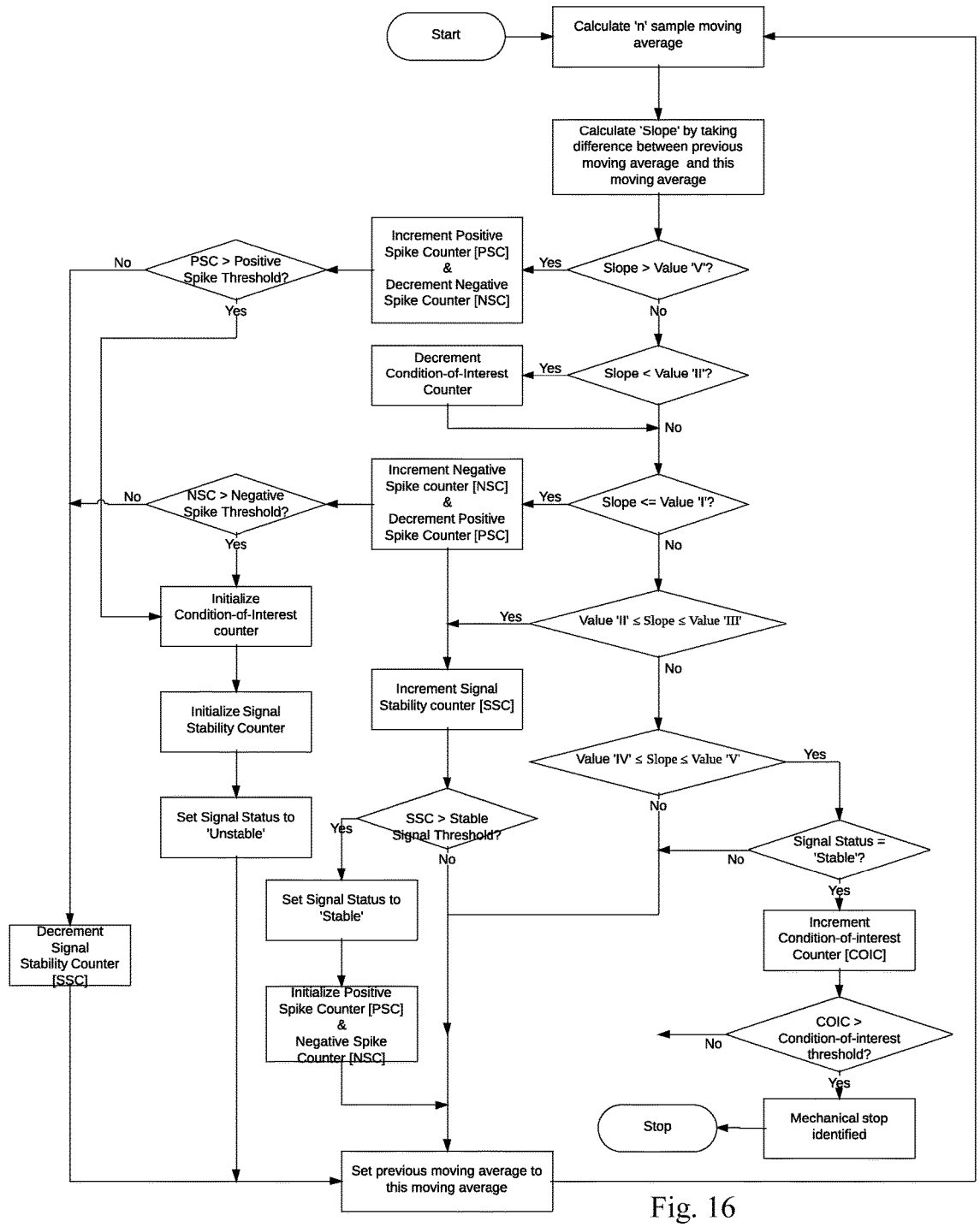
FIG. 16 is a flow chart of a method for controlling the surgical instrument of FIG. 1 according to another embodiment of the present disclosure.

FIG. 16 shows a method according another embodiment of to the present disclosure for determining if the motor 164 encounters a mechanical stop.

The controller 406 includes the stability and condition-of-interest counters, as described above. The controller 406 further includes a positive spike counter and a negative spike counter. These counters maintain a number of times a current (e.g., slope) has spiked outside the first range. More specifically, the positive spike counter is incremented when the motor current is above the value "V" and the negative spike counter is incremented when the motor current is below the value "I." The controller 406 determines if the measured rate of change current draw signal is stable using the values of the table 500. The signal is considered to be unstable if a predetermined number of current draw samples are outside the first range (e.g., is the number of positive and negative spikes is above a predetermined positive and negative spike threshold) and stable if a predetermined number of samples are within the second range.

The method of FIG. 16 may also be implemented as software instructions (e.g., algorithm) stored in the controller 406 as described above. Initially, the controller 406 calculates a moving average of the measured motor current (e.g., current draw). As used herein, the term "moving average" denotes an average of a predetermined subset of samples that is updated every time a new sample is obtained. The moving average may include from about 2 samples to about 256 samples, and in embodiments, from about 16 to about 64 samples, depending on the sampling rate described above. The controller 406 stores the first moving average and calculates the second moving average for the subsequent sample set. The controller 406 then determines the difference between the moving averages to calculate the sample-to-sample change (e.g., slope).

The change in the monitored motor current, also defined as the slope, is used to differentiate between different types of loads encountered by motor 164. The controller 406 initially determines if the slope is larger than fifth value "V" and updated the previous moving average to the presently calculated moving average. If the slope is above the fifth value "V," the positive spike counter is incremented while the negative spike counter is decremented. In addition, the controller 406 verifies if the positive spike counter is above a predetermined positive spike counter threshold. If so, the controller 406 initializes or resets the condition-of-interest and signal stability counters by setting them to zero, 0. In addition, the controller 406 also sets the signal status as "unstable." If the positive spike counter is below the predetermined positive spike counter threshold, the stability counter is decremented.

After determining if the slope is above the fifth value "V," the controller 406 determines if the sample falls below second value "II," the condition-of-interest counter is decremented.

The controller 406 also determines if the slope is smaller than the first value "I" and updated the previous moving average to the presently calculated moving average. If the slope is above the first value "I," the negative spike counter is incremented while the positive spike counter is decremented. In addition, the controller 406 verifies if the negative spike counter is above a predetermined negative spike counter threshold. If so, the controller 406 initializes or resets the condition-of-interest and signal stability counters by setting them to zero, 0. In addition, the controller 406 also sets the signal status as "unstable." If the negative spike counter is below the predetermined negative spike counter threshold, the stability counter is decremented.

With reference to FIGS. 14 and 15, the samples below first value "I," as shown in FIG. 14, and above the fifth value "V," as shown in FIG. 15, are filtered out since they represent abnormal negative and positive spikes in current draw. These spikes may be caused by starting and stopping of the motor 164 and may result false positives in threshold-based decision making algorithms.

The controller 406 also determines if the slope is within the second range (e.g., value "II"≤slope≤value "III"). If so, the stability counter is incremented. The controller 406 also checks if the stability counter has reached a predetermined threshold before changing the signal status to "stable." This ensures that the sample has been within the second range for a sufficient period of time. In addition, the controller 406 initializes or resets the positive and negative spike counters by setting them to zero, 0. Regardless whether the stability counter is below or above the predetermined threshold, the previous moving average is updated to the presently calculated moving average. Any deviation, e.g., the slope being outside the first range, also resets the condition-of-interest and signal stability counters and sets the signal status as "unstable" as described above.

The controller 406 also determines if the sample is within the third range. For each sample within the third range, while the signal is deemed stable, the condition-of-interest counter is incremented. The condition-of-interest counter is used to identify a mechanical stop, as described in further detail below. If the condition-of-interest counter is above a predetermined threshold, then the controller 406 determines that a mechanical stop has been reached. With reference to FIG. 13, a plurality of samples have a slope that falls within the third range, this increments the condition-of-interest counter and upon reaching the predetermined count triggers the indication that the mechanical stop has been reached. Once the controller 406 determines that the mechanical limit has been reached the supply of current to the motor 164 may be terminated to prevent further operation of the instrument 100 and/or the instrument 100 may issue an alarm.

In addition to basic feedback about device performance the present disclosure also provides a method for powered devices to detect and discern other external factors, e.g., thicker tissue, which previously were difficult to detect. As a result, improved cutoffs and values for limits can be implemented, greatly improving the safety of powered devices in use. Using the feedback mechanisms discussed above, users may make intelligent decisions about what settings and techniques should be used when operating the instrument 100. This intelligence can range from choosing a different reload to fire with a linear stapler, deciding to fire at a different articulation angle, to choosing to use a completely different surgical technique.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A method for controlling a surgical instrument comprising:
   monitoring a current draw of a motor coupled to a drive assembly for actuating a jaw assembly of the surgical instrument;
   calculating a plurality of rate of change values based on a plurality of samples of the current draw; and
   continuously determining whether the motor has reached a mechanical limit based on whether the plurality of rate of change values are within a first range and whether the current draw of the motor is stable based on the plurality of rate of change values being within a second range,
   wherein the first range corresponds to the motor reaching the mechanical limit and the second range corresponds to stable operation of the motor.

2. The method according to claim 1, further comprising: determining whether the current draw of the motor is unstable based on the plurality of rate of change values being within a third range.

3. The method according to claim 2, further comprising:
   storing a stability counter of rate of change values calculated as being within the second range; and
   determining whether operation of the motor is stable when the stability counter is above a predetermined stability threshold.

4. The method according to claim 3, wherein the first range is within the second range and the third range is higher than the second range.

5. The method according to claim 3, further comprising:
   storing an event counter of rate of change values within the third range; and determining whether the motor is unstable when the event counter is above a predetermined event threshold.

6. The method according to claim 1, further comprising: controlling the current draw of the motor for actuating the jaw assembly of the surgical instrument.

7. The method according to claim 6, wherein controlling includes reducing the current draw of the motor based on a determination that the motor has reached a mechanical limit.

* * * * *